(12) United States Patent
Cummings et al.

(10) Patent No.: US 12,220,311 B2
(45) Date of Patent: Feb. 11, 2025

(54) MINIMALLY INVASIVE MAGNETIC VOCAL FOLD MANIPULATOR

(71) Applicant: The Johns Hopkins University, Baltimore, MD (US)

(72) Inventors: Charles W. Cummings, Baltimore, MD (US); Allen L. Feng, Baltimore, MD (US); Christopher Razavi, Baltimore, MD (US); Alexander T. Hillel, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 690 days.

(21) Appl. No.: 17/604,650

(22) PCT Filed: Apr. 17, 2020

(86) PCT No.: PCT/US2020/028714
§ 371 (c)(1),
(2) Date: Oct. 18, 2021

(87) PCT Pub. No.: WO2020/214927
PCT Pub. Date: Oct. 22, 2020

(65) Prior Publication Data
US 2022/0183822 A1  Jun. 16, 2022

Related U.S. Application Data

(60) Provisional application No. 62/836,141, filed on Apr. 19, 2019.

(51) Int. Cl.
*A61F 2/20* (2006.01)

(52) U.S. Cl.
CPC .......... *A61F 2/20* (2013.01); *A61F 2210/009* (2013.01); *A61F 2220/0025* (2013.01); *A61F 2220/0041* (2013.01)

(58) Field of Classification Search
CPC ............................ A61F 2/20; A61M 2210/065
See application file for complete search history.

(56) References Cited

U.S. PATENT DOCUMENTS

| | | | |
|---|---|---|---|
| 5,593,439 A | 1/1997 | Cummings et al. | |
| 7,069,082 B2 | 6/2006 | Lindenthaler | |
| 7,212,639 B1* | 5/2007 | Houston | A61F 2/20 381/70 |
| 8,136,532 B2 | 3/2012 | Lindenthaler et al. | |

(Continued)

OTHER PUBLICATIONS

International Search Report and Written Opinion for PCT/US20/28714. Mailed Jul. 21, 2020. 14 pages.

(Continued)

*Primary Examiner* — Melanie R Tyson
*Assistant Examiner* — Yasniary De La Caridad Morales
(74) *Attorney, Agent, or Firm* — Casimir Jones, S.C.; Brian F. Bradley

(57) ABSTRACT

A minimally invasive magnetic vocal fold manipulator system and method is disclosed. Namely, a magnetic vocal fold manipulator system is provided that includes a magnetics-based thyroid cartilage implant, a magnetics-based arytenoid cartilage implant, and an implant introducer device. Additionally, a method is provided of using the minimally invasive magnetic vocal fold manipulator system for performing lateralization and/or medialization of the vocal cord.

35 Claims, 26 Drawing Sheets

(56) References Cited

U.S. PATENT DOCUMENTS

| | | | |
|---|---|---|---|
| 2013/0245639 A1* | 9/2013 | Lindenthaler | A61N 1/0519 606/129 |
| 2014/0336761 A1* | 11/2014 | Schaeffer | A61F 2/20 623/14.11 |
| 2014/0364915 A1 | 12/2014 | Culbert et al. | |
| 2018/0303603 A1* | 10/2018 | Melsheimer | A61F 2/20 |
| 2018/0303605 A1 | 10/2018 | Tanner et al. | |
| 2022/0151464 A1* | 5/2022 | Bendory | A61B 1/0058 |

OTHER PUBLICATIONS

Ciftci et al., Magnetic Control of the Glottic Opening in an Ex Vivo Sheep Larynx Model: A Preliminary Study. J Voice. Sep. 2016;30(5):621-5.

Cummings et al., Minimally invasive device to effect vocal fold lateralization. Ann Otol Rhinol Laryngol. Sep. 1999;108(9):833-6.

Li et al., Current Treatment Options for Bilateral Vocal Fold Paralysis: A State-of-the-Art Review. Clin Exp Otorhinolaryngol. Sep. 2017;10(3):203-212.

Mueller et al., Laryngeal pacing via an implantable stimulator for the rehabilitation of subjects suffering from bilateral vocal fold paralysis: A prospective first-in-human study. Laryngoscope. Aug. 2016;126(8):1810-6.

Ohta et al., Vocal cord paralysis after aortic arch surgery: predictors and clinical outcome. J Vasc Surg. Apr. 2006;43(4):721-8.

Sulica et al., Preface in Vocal Fold Paralysis. Springer, New York. 2006. 13 pages.

Young et al., Analysis of laryngeal framework surgery: 10-year follow-up to a national survey. Laryngoscope. Aug. 2010;120(8):1602-8.

* cited by examiner

MINIMALLY INVASIVE MAGNETIC VOCAL FOLD MANIPULATOR

BACKGROUND

Unilateral vocal fold paralysis is a relatively common disorder. For example, approximately 166,000 patients undergo thyroid surgery in the United States yearly with a reported 9.5% complication rate of vocal fold paralysis. Moreover, there were at least 29,748 medialization thryoplasty procedures (an operation performed for treating vocal fold paralysis) completed between 1998-2008. Notably these values do not encompass the total number of cases yearly, as vocal fold paralysis is a potential surgical complication that extends to other specialties, including, but not limited to, cardiothoracic surgery. For instance, in aortic arch surgery alone, estimated rates of vocal cord paralysis as a post-operative complication are in excess of 20%.

The exact incidence of unilateral vocal fold paralysis is unknown due to the difficulty in detecting the condition and the interpretation of findings, as well as a lack of patient presentation to care. Methods known in the art for correcting the deficit of a compromised airway created, for example, from bilateral abductor paralysis, are invasive, irreversible, and can often destroy the vocal fold tissue. In such procedures, surgical removal of the arytenoid cartilage is achieved through a translaryngeal approach (operating laryngoscope) or an external (transcervical) approach. A laser is commonly used to remove the cartilage via a "keyhole" procedure, wherein an initial cut perpendicular to the long axis of the vocal fold is created and extended in a circular fashion. These procedures can create a better airway, but can sacrifice the quality of a patient's voice.

Alternative procedures have been proposed, where the vocal cord is displaced laterally through an external mechanism to improve the quality of the airway. One such procedure involves the use of a suture to transverse the thyroid cartilage, extending medially to the arytenoid cartilage, and then subsequently back to the thyroid cartilage. Lateral traction in this instance allows for the lateralization of the vocal cord. This type of procedure, however, is not reversible or adjustable. Other more recent systems have involved the mechanical fixation of the arytenoid cartilage to an external component located on the thyroid cartilage. The components described in this system and others known in the art, however, are not easily adjustable or reversible. The depth at which the components must be introduced also increases the odds of post-operative complications, including fistula formation.

SUMMARY

In some aspects, the presently disclosed subject matter provides a device for manipulating a position of a vocal fold of a subject comprising: (a) a thyroid cartilage implant comprising a magnet housed in body, wherein the body is seated within a translational bushing mated to an anchoring flange, wherein the anchoring flange is adapted to be affixed to a thyroid cartilage of the subject; and (b) an arytenoid screw adapted to be affixed to an arytenoid cartilage of the subject.

In certain aspects of the presently disclosed device, the magnet can be a permanent magnet or an electromagnet. In particular aspects, the permanent magnet comprises a neodymium magnet.

In certain aspects, the body of the presently disclosed device comprises a hollow tubular body having a slotted end and an opposite non-slotted end. In certain aspects, the translational bushing comprises a hollow tubular bushing having a slotted end and an opposite threaded end. In more certain aspects, the opposite threaded end of the translational bushing comprises a plurality of male threads adapted for mating with the anchoring flange.

In certain aspects, the anchoring flange comprises a hollow tubular flange having a plurality of threads on an inner surface thereof. In more certain aspects, the plurality of threads on the inner surface of the anchoring flange comprise female threads adapted for mating with the translational bushing. In yet more certain aspects, the translational bushing is adapted to move axially with respect to the anchoring flange.

In certain aspects, one or more of the body, the translational bushing, and the anchoring flange comprises a material selected from the group consisting of consisting of cobalt-chrome, stainless steel, titanium, a polymeric material, and medical grade silicone.

In certain aspects, the arytenoid screw comprises one or more components selected from the group consisting of a shaft, a beveled and hollowed tip mounted on one end of the shaft, and a slotted flange on an opposite end of the shaft. In more certain aspects, the beveled and hollowed tip further comprises two 90-degree sections on complementary sides thereof. In yet more certain aspects, the arytenoid screw comprises one or more of a magnetizable material or a magnet.

In certain aspects, the device further comprises an implant introducer device. In particular aspects, the implant introducer device comprises a handle grip operatively coupled to an elongated hollow chamber that houses a component selected from a custom screwdriver, and a custom puncture tool. In more particular aspects, the custom screwdriver comprises a flattened Phillips head screwdriver or a slot head screwdriver. In yet more particular aspects, the elongated hollow chamber of the implant introducer device further comprises a magnetized or magnetizable arytenoid locking screw.

In other aspects, the magnet comprises an electromagnet. In such aspects, the device further comprises a laryngeal pacing system.

In certain aspects, the presently disclosed subject matter provides a kit for manipulating a position of a vocal fold, comprising the thyroid cartilage implant and the magnetics-based arytenoid cartilage implant described hereinabove. In certain aspects, the kit further comprises an implant introducer device. In more certain aspects, the kit further comprises one or more components selected from one or more custom screwdrivers, a custom puncture tool, and instructions for use.

In certain aspects, the presently disclosed subject matter provides a method for manipulating a position of a vocal fold of a subject, the method comprising: (a) providing a presently disclosed device for manipulating a position of a vocal fold of a subject or a presently disclosed kit; (b) implanting the thyroid cartilage implant in a thyroid cartilage of the subject; (c) implanting the arytenoid screw in an arytenoid cartilage of the subject; and (d) adjusting a position of the magnet of the thyroid cartilage implant relative to the arytenoid screw to engage the arytenoid screw, thereby manipulating a position of the vocal fold of the subject.

In certain aspects, the arytenoid screw is implanted into the arytenoid cartilage via a translaryngeal approach. In more certain aspects, the implanting of the arytenoid screw comprises raising a mucosal flap over an ipsilateral arytenoid complex of the subject and affixing the arytenoid screw to the arytenoid cartilage. In yet more certain aspects, the arytenoid screw is turned about 90 degrees to mechanically fix it to the arytenoid cartilage. In certain aspects, the method is performed under direct visualization to confirm placement of the thyroid cartilage implant and/or arytenoid screw. In more certain aspects, the visualization is performed via translaryngeal endoscopy.

In other certain aspects, the arytenoid screw may be implanted into the arytenoid cartilage via a transcervical approach. In more certain aspects, a transcervically accessed hole through the thyroid cartilage is enlarged to directly place the arytenoid screw into the underlying arytenoid cartilage. In this fashion, the arytenoid screw will remain submucosal during its implantation as it does not penetrate the endoluminal aspect of the mucosa. In yet more certain aspects, confirmation for placement of this arytenoid screw is performed through direct visualization of the glottis from above using an operating laryngoscope and operating microscope.

In more certain aspects of the presently disclosed methods, the implanting of the thyroid cartilage implant into the thyroid cartilage of the subject comprises: (a) mechanically affixing the anchoring flange to the thyroid cartilage through an iatrogenic opening of the thyroid cartilage; (b) mating the translational bushing to the anchoring flange; (c) fitting the body comprising the magnet into the translational bushing; and (d) adjusting a position of the translational bushing relative to magnetically engage the arytenoid screw, thereby manipulating a position of the vocal fold of the subject.

In yet more certain aspects, the presently disclosed method further comprises reversing a polarity of the magnet to medialize the position of the vocal fold of the subject. In such aspects, the method further comprises an electromagnet and a laryngeal pacing system for dynamic vocal fold manipulation.

Certain aspects of the presently disclosed subject matter having been stated hereinabove, which are addressed in whole or in part by the presently disclosed subject matter, other aspects will become evident as the description proceeds when taken in connection with the accompanying Drawings as best described herein below

BRIEF DESCRIPTION OF THE DRAWINGS

Figure 1:
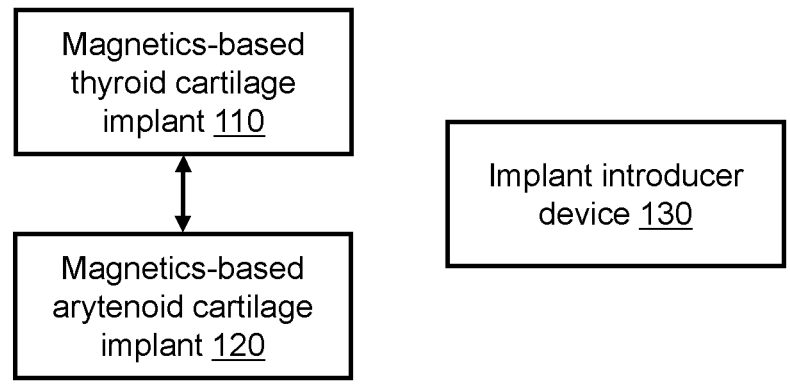
Figure 2:
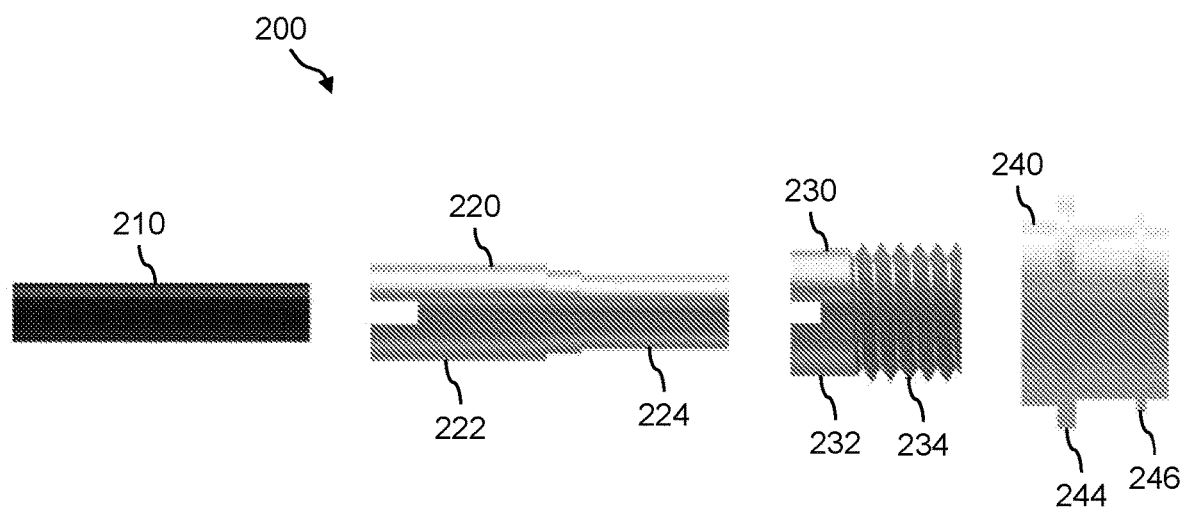
Figure 3:
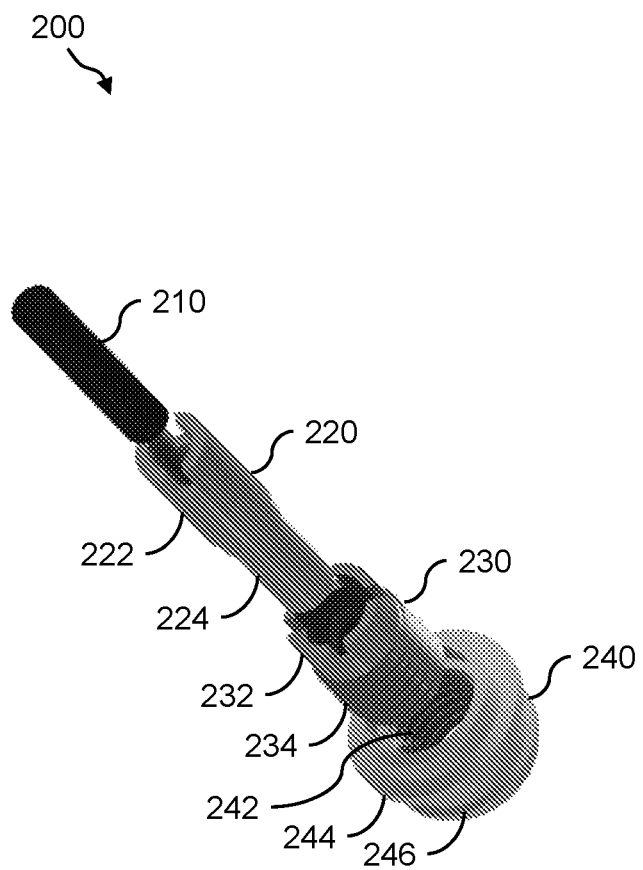
Figure 4:
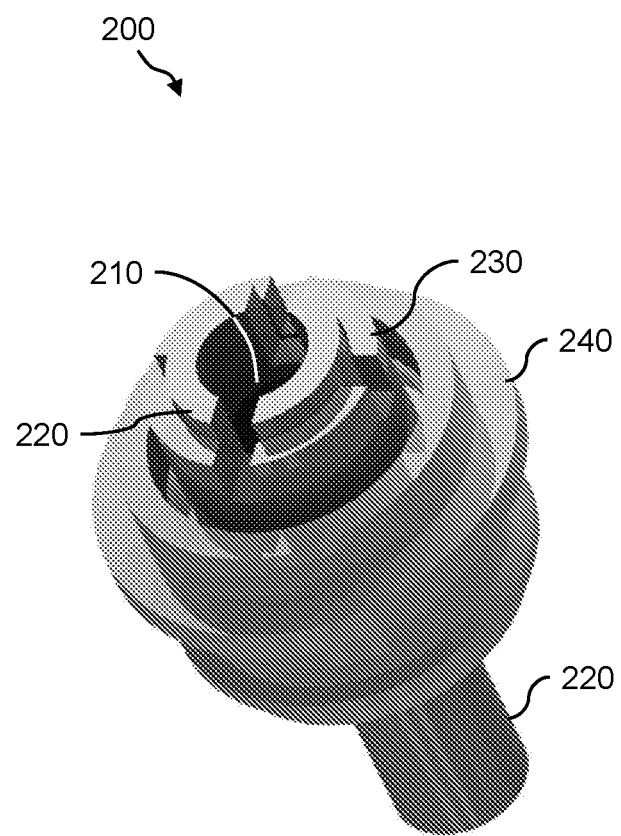
Figure 5:
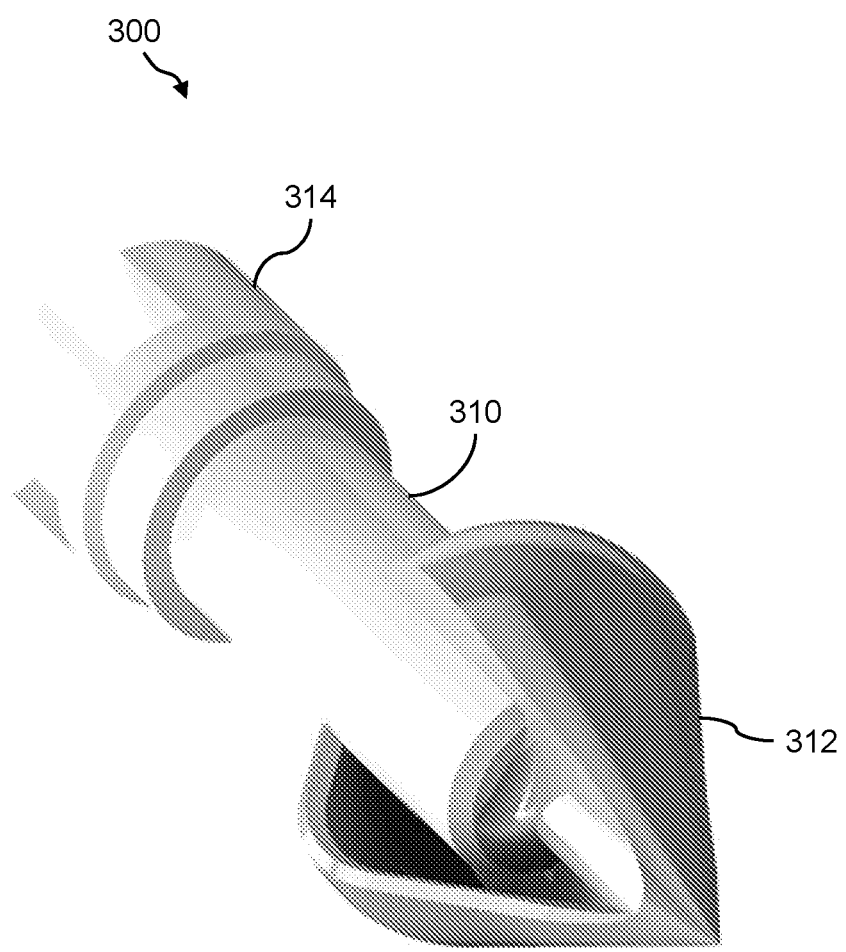
Figure 6:
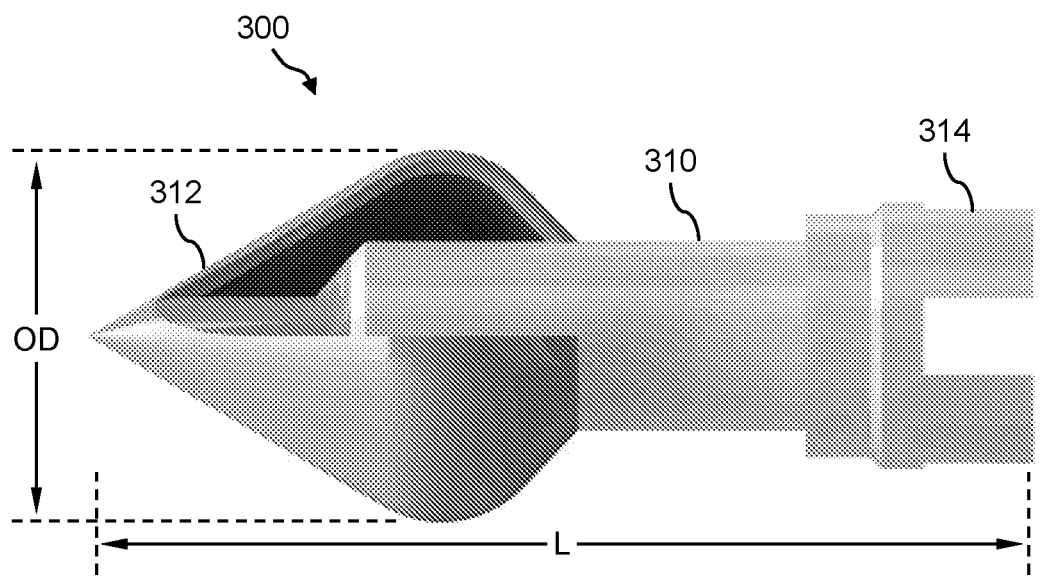
Figure 7:
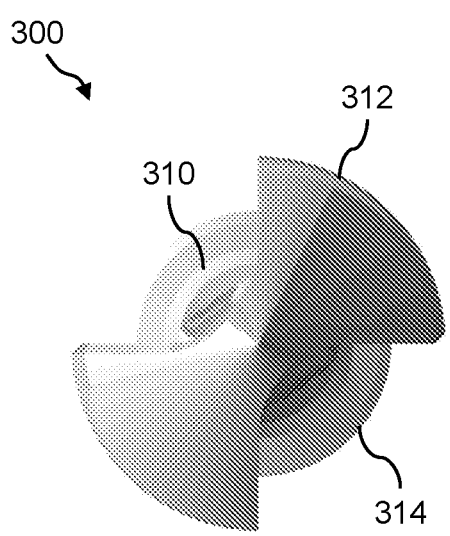
Figure 8:
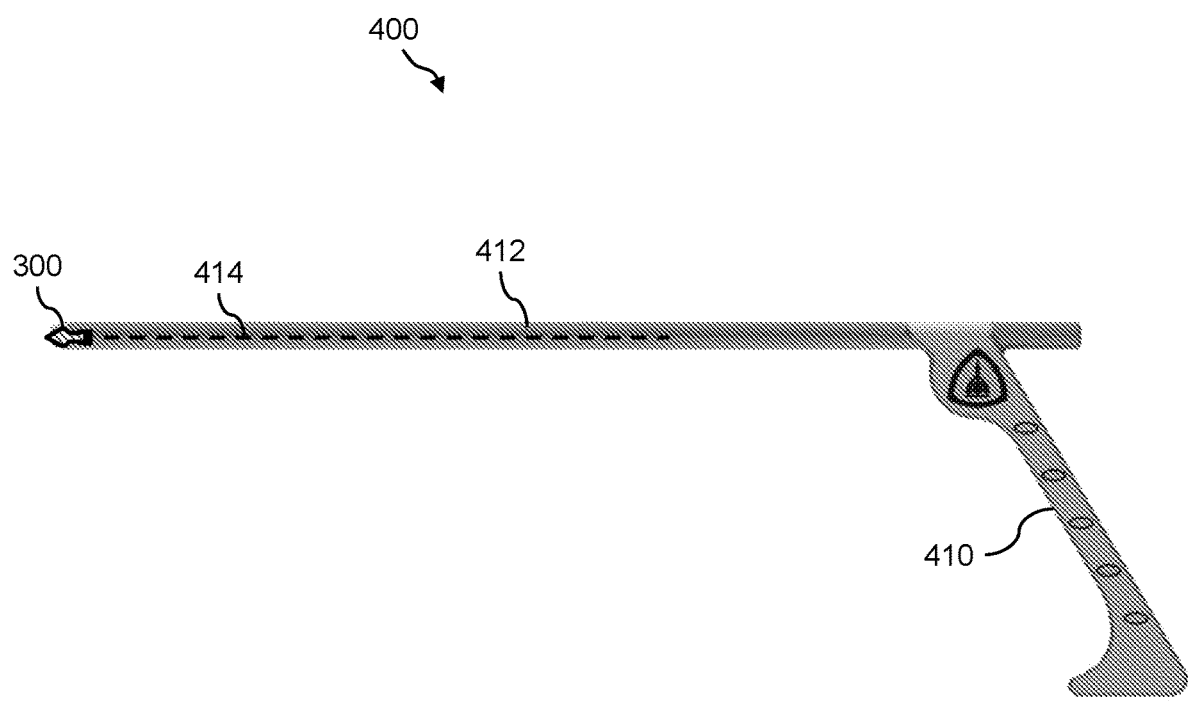
Figure 9:
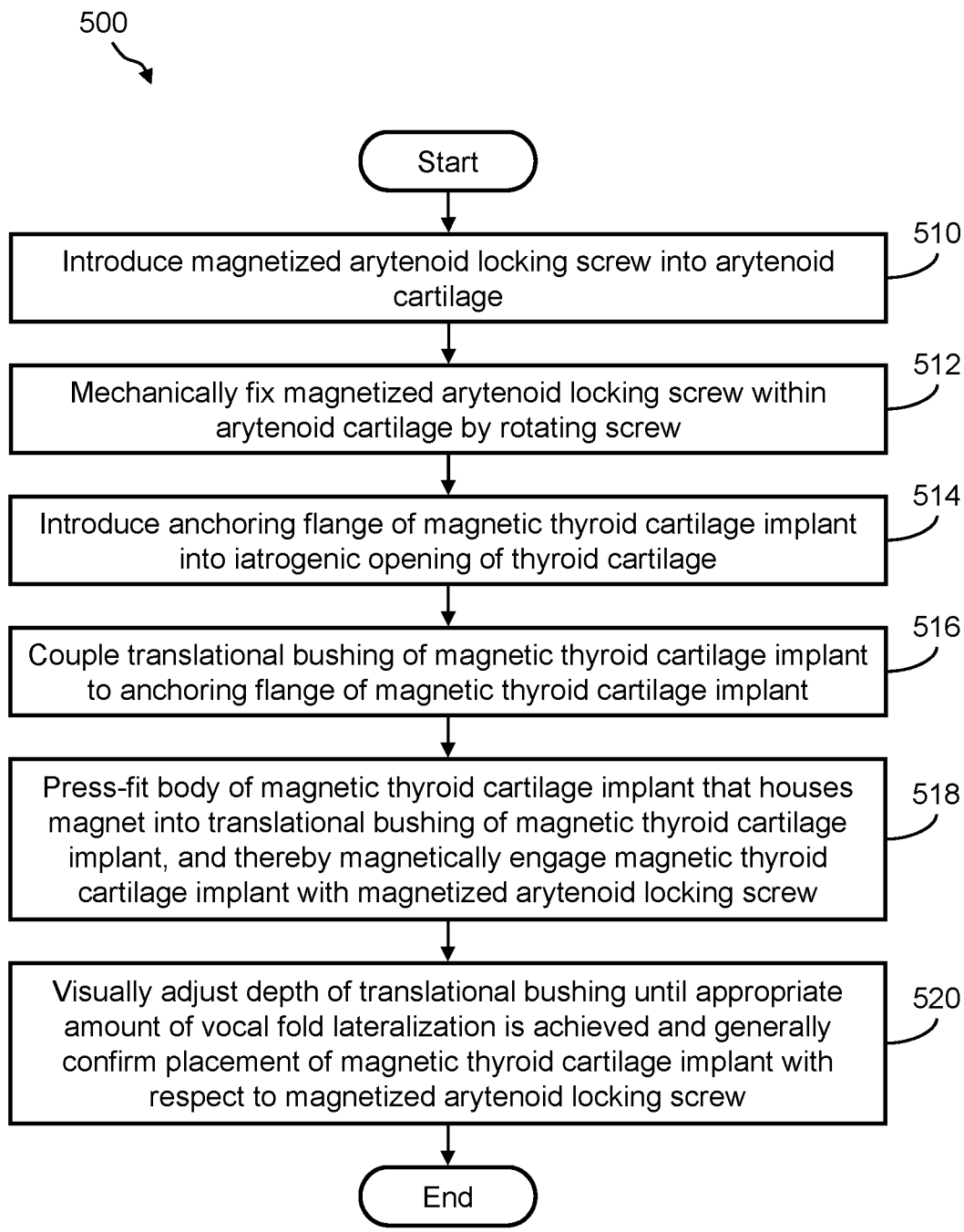
Figure 10:
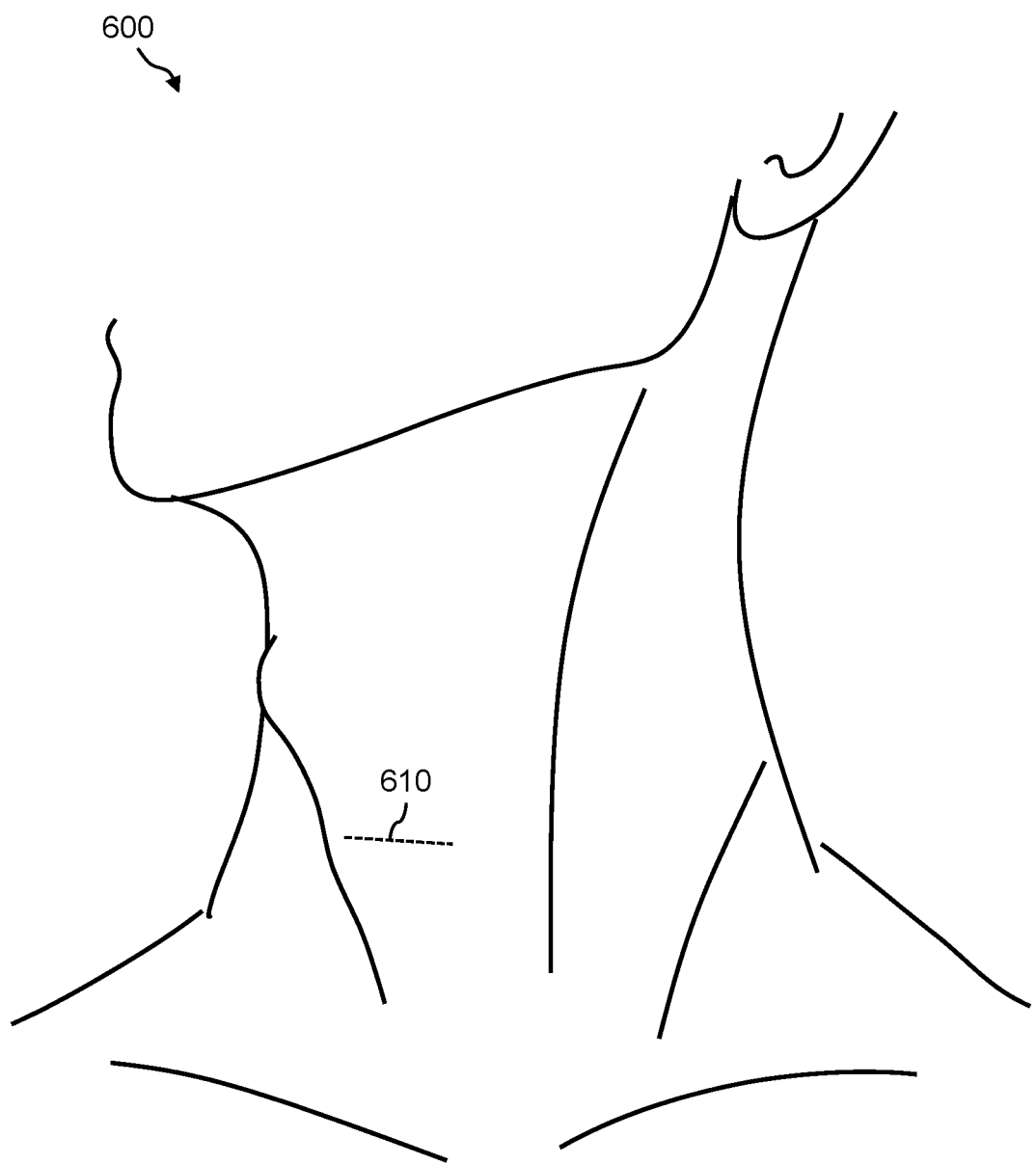
Figure 17:
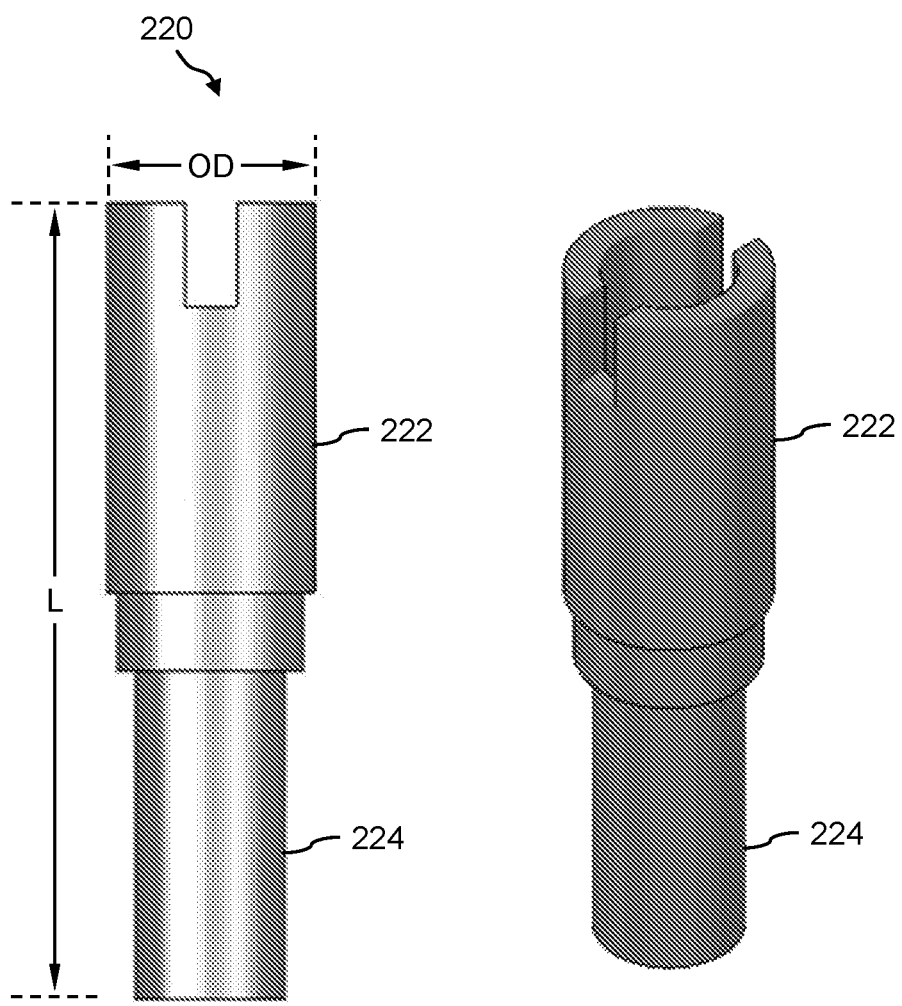
Figure 18:
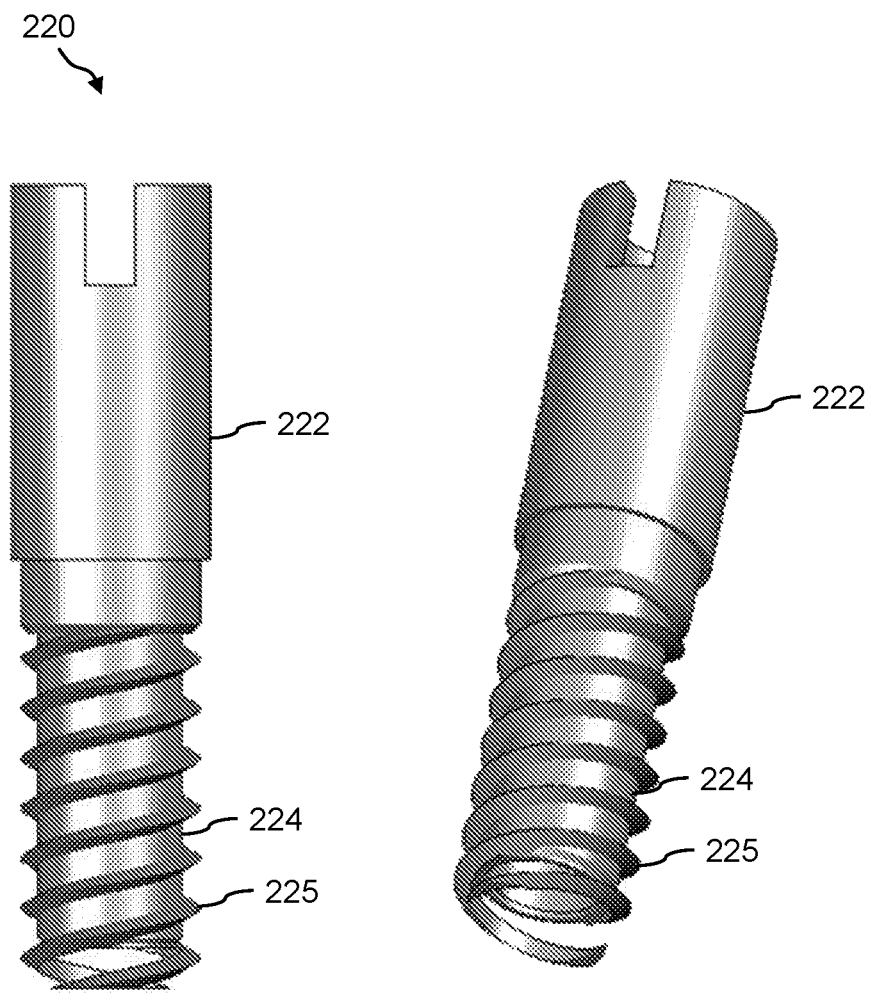
Figure 19:
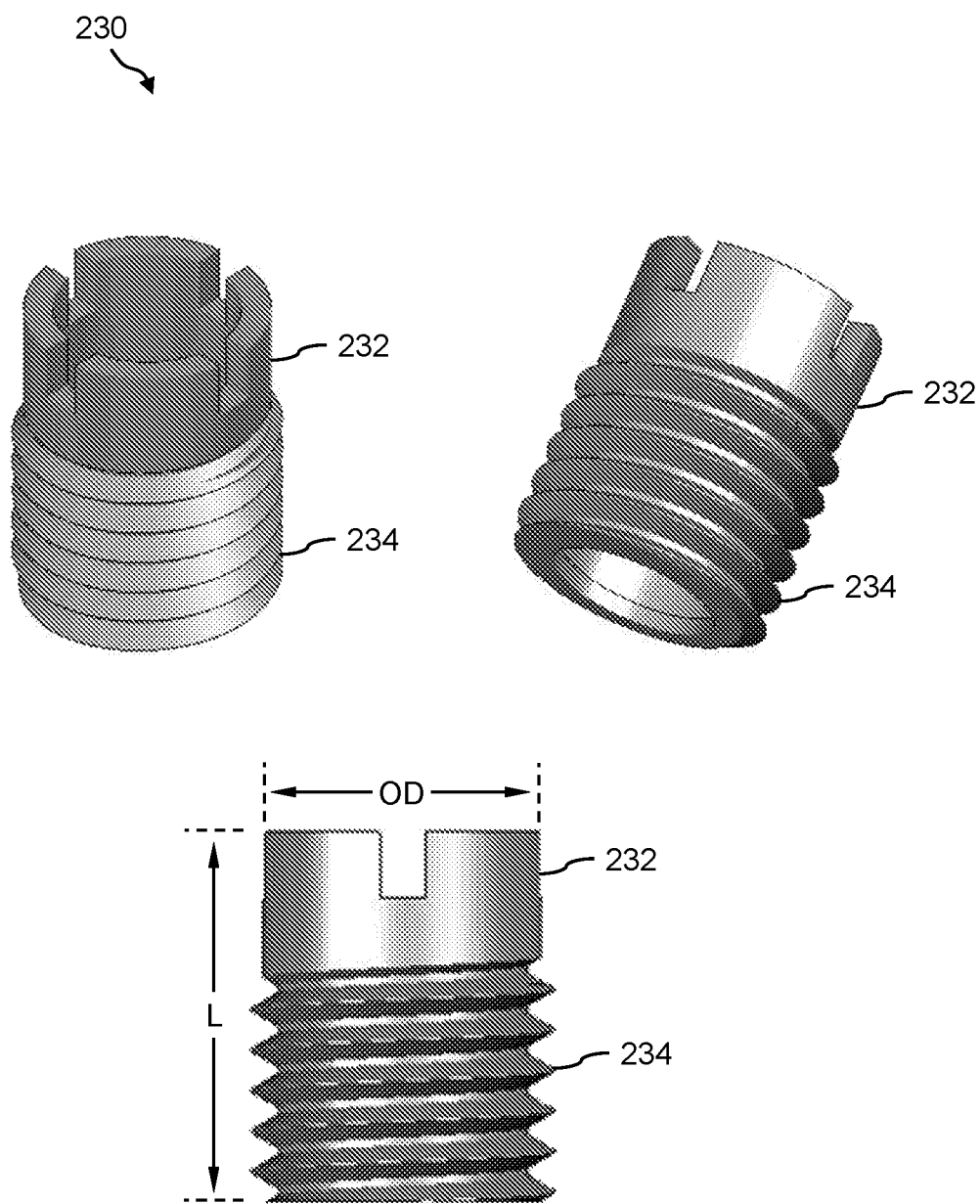
Figure 20:
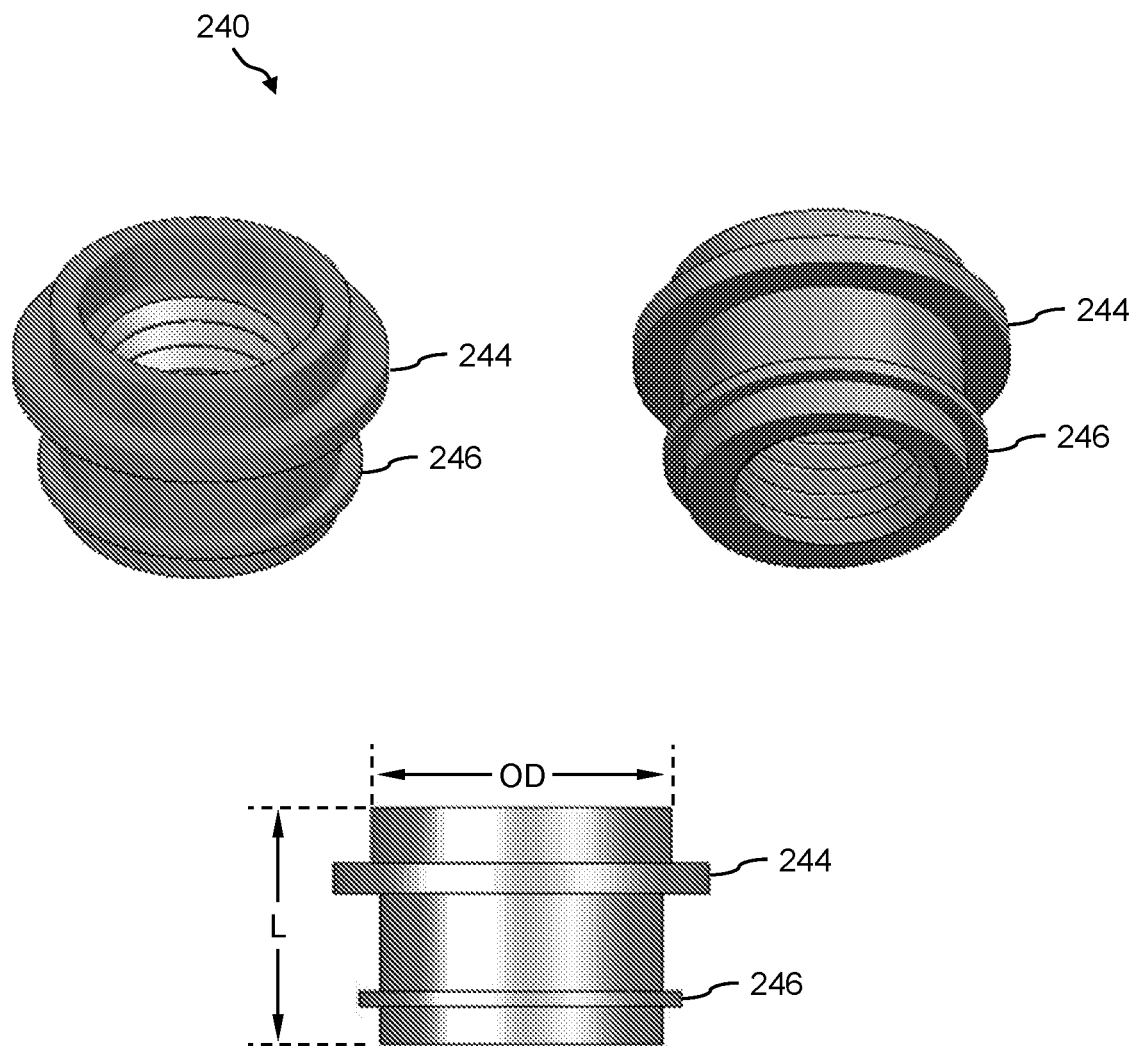
Figure 21:
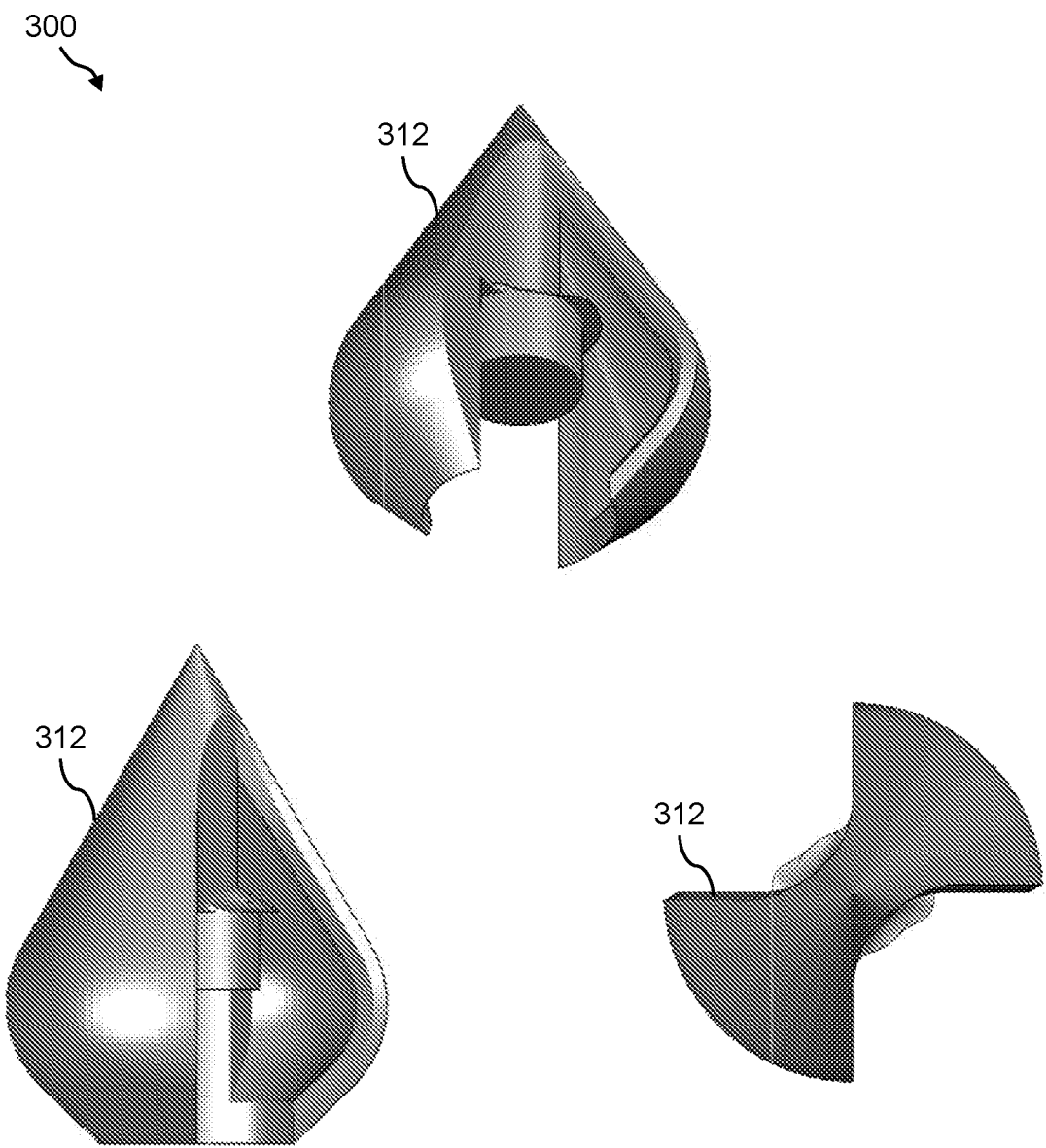
Figure 22:
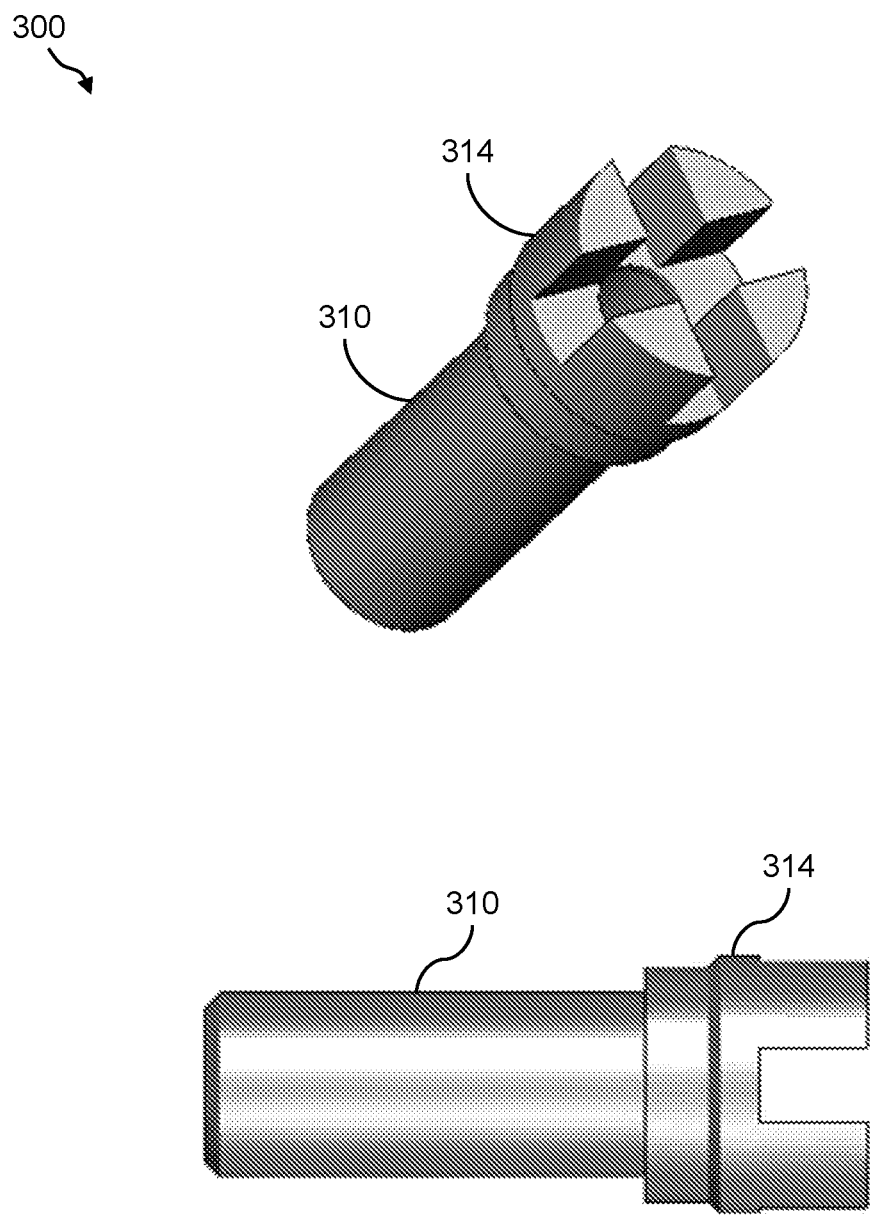
Figure 23:
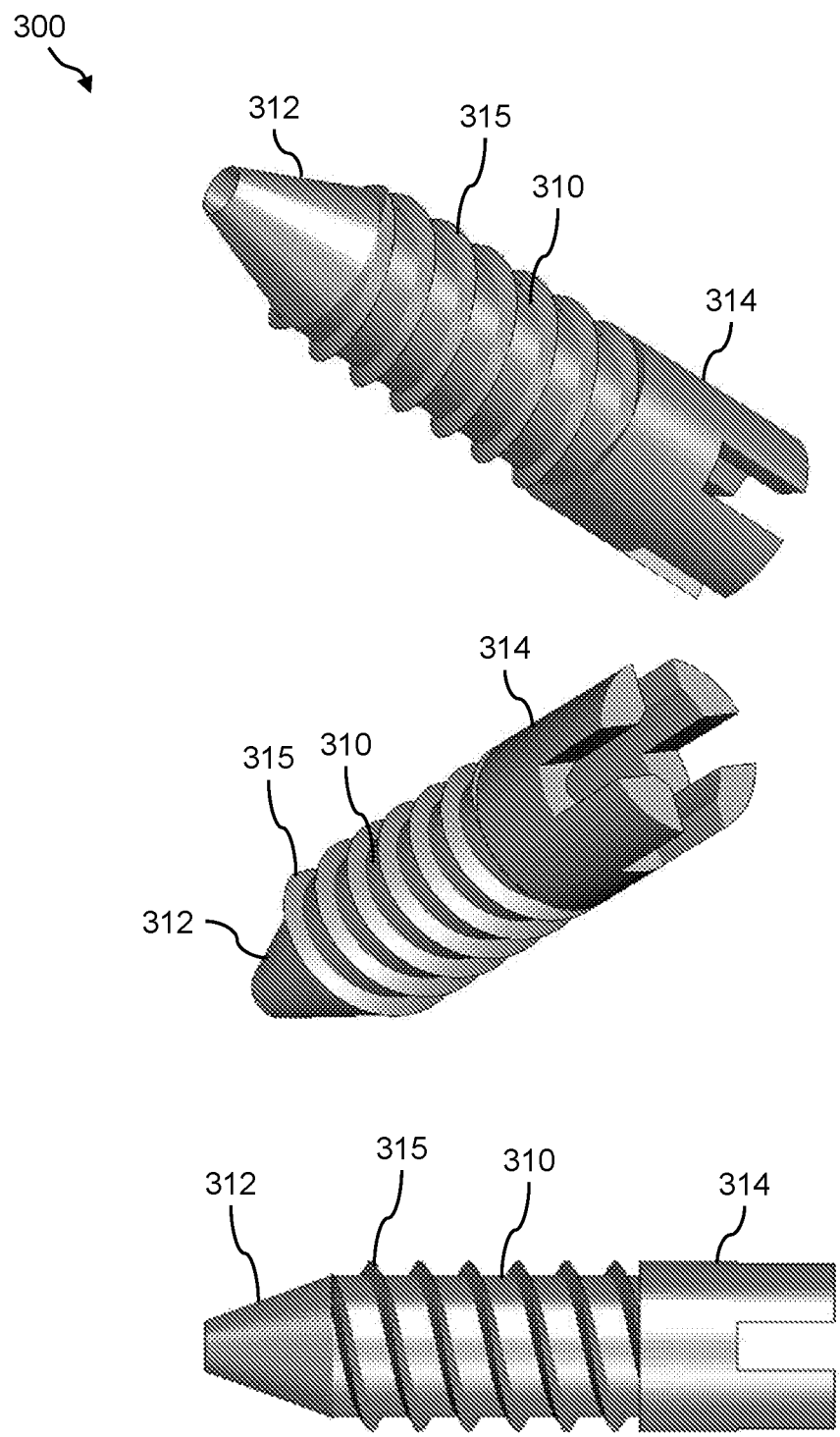
Figure 24:
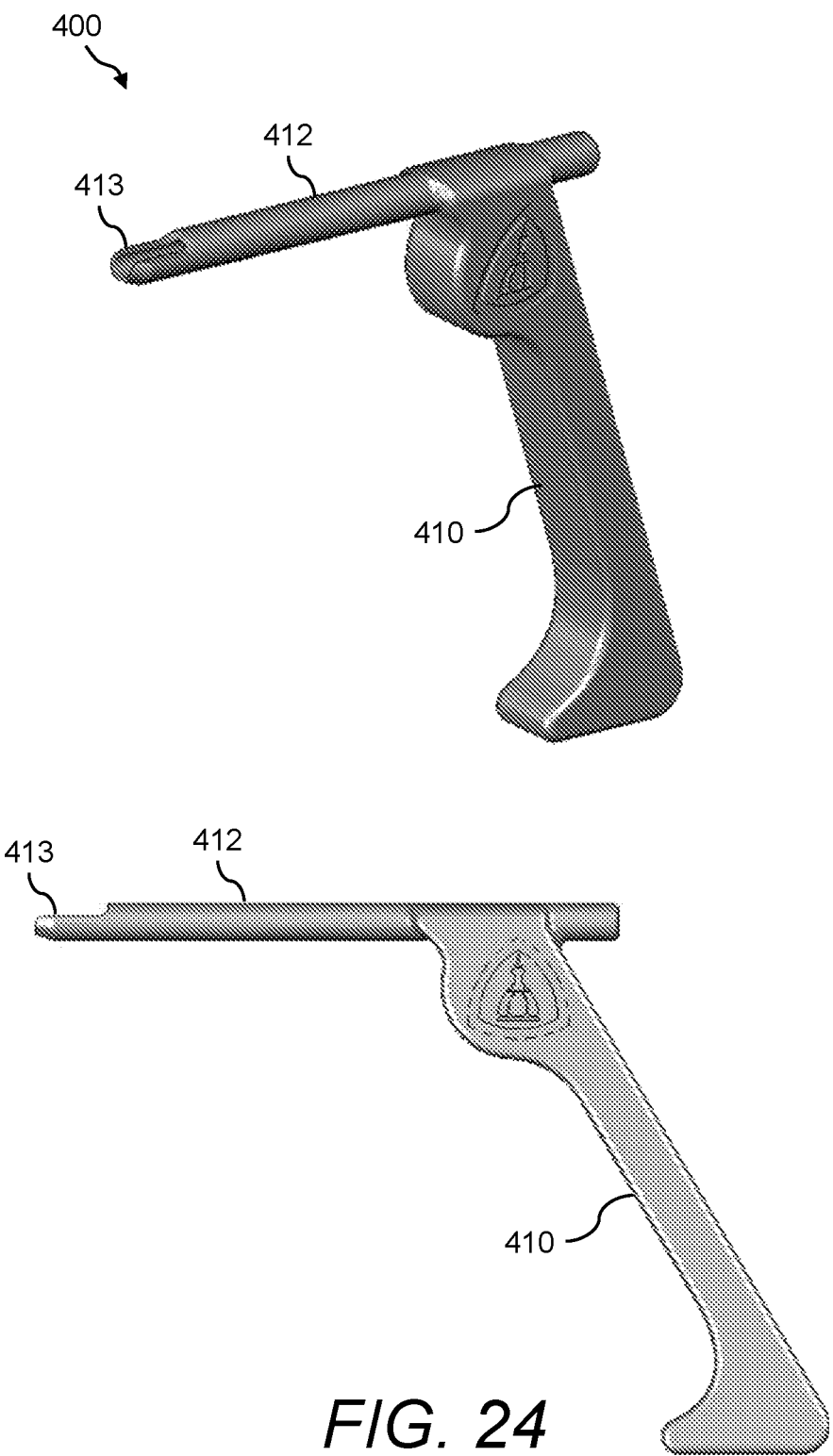
Figure 25:
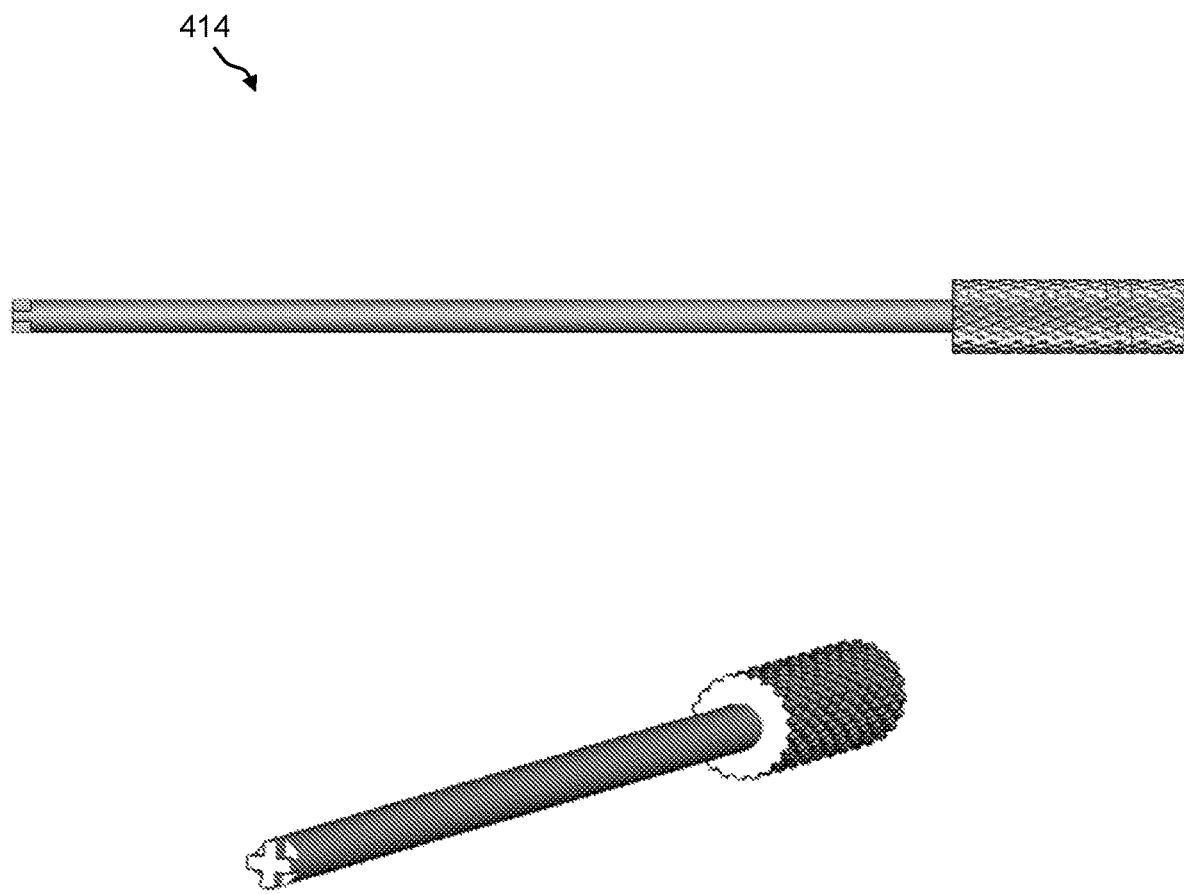
Figure 26:
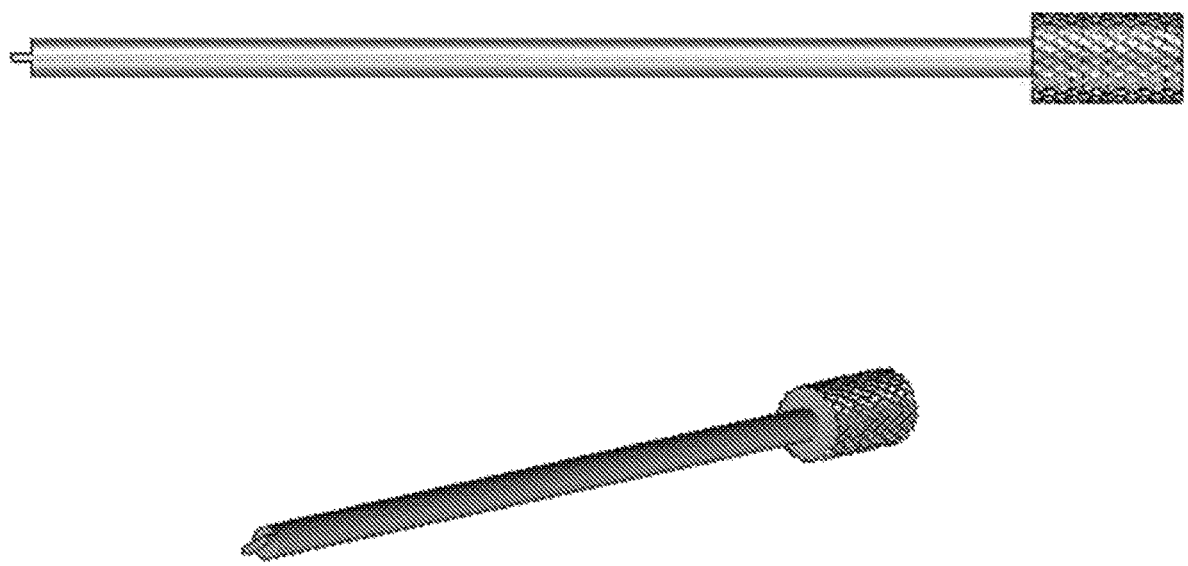
Figure 27:
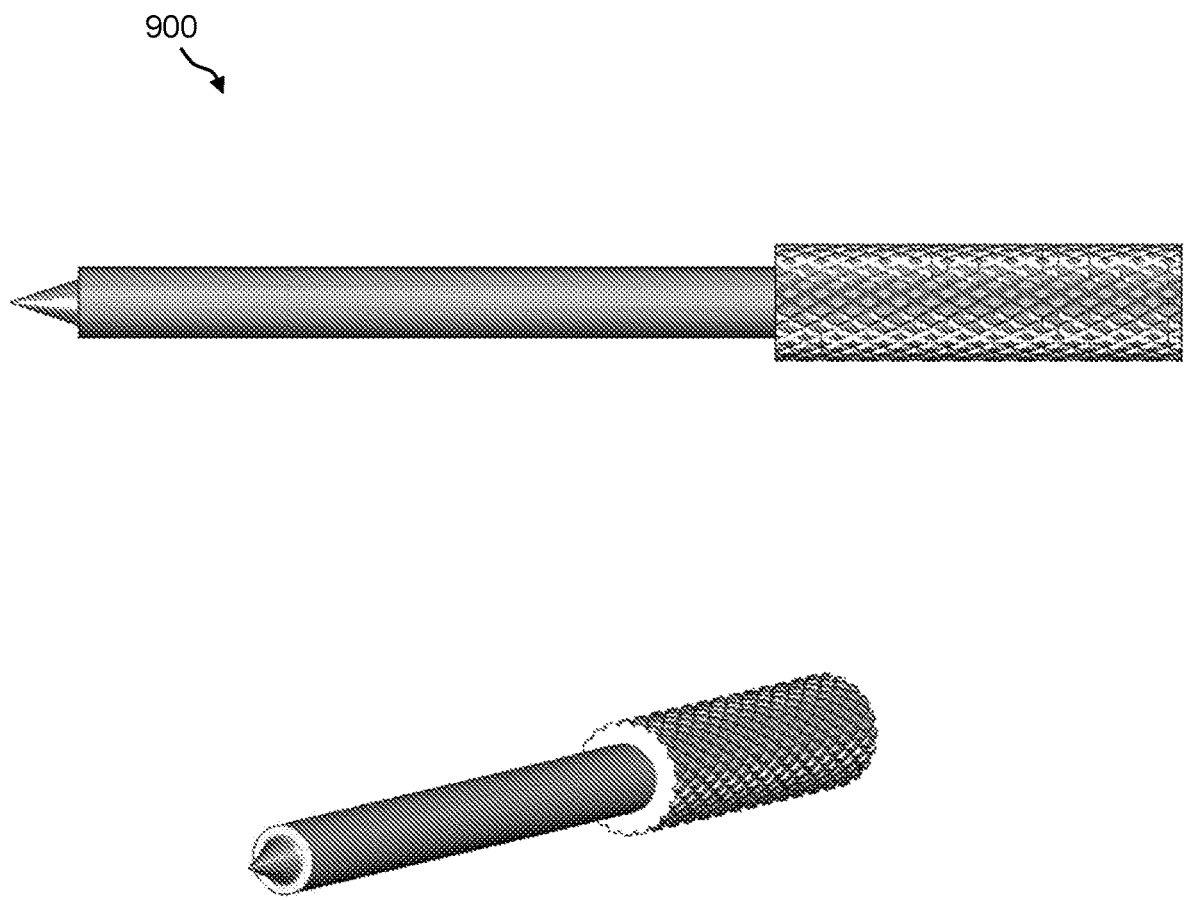

Having thus described the presently disclosed subject matter in general terms, reference will now be made to the accompanying Drawings, which are not necessarily drawn to scale, and wherein:

FIG. 1 illustrates a block diagram of an example of the presently disclosed magnetic vocal fold manipulator system that includes a magnetics-based thyroid cartilage implant, a magnetics-based arytenoid cartilage implant, and an implant introducer device;

FIG. 2, FIG. 3, and FIG. 4 illustrate an exploded side view, an exploded perspective view, and a perspective view, respectively, of a magnetic thyroid cartilage implant, which is an example of the magnetics-based thyroid cartilage implant shown in FIG. 1, illustrating the orientation of each component relative to the other components of the presently disclosed magnetics-based thyroid cartilage implant;

FIG. 5, FIG. 6, and FIG. 7 illustrate a perspective view, a side view, and a front view, respectively, of an implantable magnetized arytenoid locking screw, which is an example of the magnetics-based arytenoid cartilage implant shown in FIG. 1;

FIG. 8 illustrates a side view of a vocal cord lateralization device introducer, which is an example of the implant introducer device shown in FIG. 1;

FIG. 9 illustrates a flow diagram of an example of a method of using the presently disclosed magnetic vocal fold manipulator system for performing lateralization and/or medialization of the vocal cord;

FIG. 10 illustrates a front view of the subject of a vocal fold manipulation procedure and an example of the incision therefor;

FIG. 11 through FIG. 16 illustrate various views of the vocal anatomy showing an example of the process of using the presently disclosed magnetic vocal fold manipulator system for performing lateralization and/or medialization of the vocal cord;

FIG. 17 illustrates a side view and a perspective view showing more details of the body of the magnetic thyroid cartilage implant shown in FIG. 2, FIG. 3, and FIG. 4, which is a non-threaded body;

FIG. 18 illustrates a side view and a perspective view of another example of the body of the magnetic thyroid cartilage implant, which is a threaded body;

FIG. 19 illustrates a side view and a perspective view showing more details of the translational bushing of the magnetic thyroid cartilage implant shown in FIG. 2 and FIG. 3;

FIG. 20 illustrates a side view and a perspective view showing more details of the anchoring flange of the magnetic thyroid cartilage implant shown in FIG. 2, FIG. 3, and FIG. 4;

FIG. 21 illustrates a perspective view, a side view, and an end view showing more details of the tip portion of the arytenoid locking screw shown in FIG. 5, FIG. 6, and FIG. 7;

FIG. 22 illustrates a perspective view and a side view showing more details of the slotted flange portion of the arytenoid locking screw shown in FIG. 5, FIG. 6, and FIG. 7;

FIG. 23 illustrates perspective views and a side view of another example of the arytenoid locking screw;

FIG. 24 illustrates a perspective view and a side view of another example of the vocal cord lateralization device introducer shown in FIG. 8;

FIG. 25 illustrates a side view and a perspective view of an example of a custom screwdriver having a flattened Phillips head for use with the vocal cord lateralization device introducer;

FIG. 26 illustrates a side view and a perspective view of another example of a custom screwdriver having a slot head for use with the vocal cord lateralization device introducer; and FIG. 27 illustrates a side view and a perspective view of an example of a custom puncture tool for use with the vocal cord lateralization device introducer.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Minimally Invasive Magnetic Vocal Fold Manipulator

Vocal fold immobility, including vocal fold paralysis, is a broad term that can be used to describe an abnormal, reduced, or restricted movement of the vocal folds, i.e., the true vocal folds, also referred to herein as the vocal cords, wherein the terms are used interchangeably. Vocal fold immobility can be unilateral, in which only one vocal fold is affected, or bilateral, in which both vocal folds are affected. The abnormal movement of the vocal folds can be paretic, i.e., where some movement is present, but impaired, or paralyzed, which includes complete cessation of vocal fold movement.

Vocal fold paralysis occurs when the nerve impulses to a subject's larynx are disrupted. Possible causes of vocal fold paralysis include nerve damage encountered during surgery, including surgeries to the thyroid or parathyroid glands, esophagus, neck, and chest; neck or chest injury; stroke; cancerous or noncancerous tumors; infections, including Lyme disease, Epstein-Barr virus and herpes; and certain neurological conditions, such as multiple sclerosis or Parkinson's disease. Symptoms of vocal fold paralysis include, but are not limited to, a breathy quality to the voice; hoarseness; noisy breathing; loss of vocal pitch; choking or coughing while swallowing food, drink or saliva; the need to take frequent breaths while speaking; inability to speak loudly; loss of gag reflex; ineffective coughing; and frequent throat clearing. Treatment for vocal fold paralysis can include surgery.

In some embodiments, the presently disclosed subject matter provides a minimally invasive magnetic vocal fold manipulator system and method. More particularly, the presently disclosed subject matter provides a magnetic vocal fold manipulator system that includes a magnetics-based thyroid cartilage implant that is used in combination with a magnetics-based arytenoid cartilage implant to produce varying extents of both lateralization and medialization of the vocal fold as needed.

Importantly, the presently disclosed system is implantable, reversible, and fully adjustable. Others, see, for example, U.S. Pat. No. 5,593,439 for Vocal Cord Lateralization and Medialization Device and Method, to Cummings et al., issued Jan. 14, 1997, which is incorporated herein by reference in its entirety, have described methods of vocal fold lateralization, which are not easily reversible and create the possibility of post-operative complications including fistula formation, e.g., an abnormal connection between two body parts. No devices known in the art have provided a fully reversible, or fully adjustable method of achieving vocal fold lateralization while creating minimal stress on native tissue.

In contrast, the presently disclosed subject matter provides a multi-component device and method for manipulating, including lateralization and medialization, the vocal cord(s) in a subject afflicted with permanent vocal fold paralysis, wherein the device is fully adjustable, fully reversible, and greatly reduces the amount of tissue stress at the cricoarytenoid joint. By being fully adjustable, the presently disclosed device allows the final position of the vocal cord to be modified to enhance or maximize the quality of the subject's voice, e.g., tuned to the proper level of phonation, and airway patency following the procedure. Moreover, the presently disclosed device also allows for medialization, an additional functionality useful in management of unilateral vocal fold paralysis where voice outcomes are usually the primary concern.

More particularly, the presently disclosed device and method for vocal fold lateralization (primary function) or medialization (secondary function) of the vocal fold manipulates position of the ipsilateral arytenoid process. Unlike other vocal fold lateralization devices known in the art, the presently disclosed device engages the arytenoid via a magnetic implant to pull (lateralization) or push (medialization) the cartilage or soft tissue of the vocal fold.

As used herein, the term "lateralization," and grammatical variations thereof, refers to a procedure in which a vocal fold, or the arytenoid cartilage to which the vocal fold is attached, is moved laterally to open the airway of a subject.

As used herein, the term "medialization," and grammatical variations thereof, refers to a procedure in which a vocal fold is moved or positioned toward the middle of the airway, i.e., toward a midline of the larynx, so that the functioning vocal fold can close as necessary for normal voice and swallowing function.

Accordingly, in some embodiments, the magnetics-based thyroid cartilage implant is a magnetic thyroid cartilage implant that includes a magnet and the magnetics-based arytenoid cartilage implant is an implantable magnetized or magnetizable arytenoid locking screw formed of magnetically responsive material. As a result, the presently disclosed system creates an adjustable and easily reversible system that minimizes the destruction/disruption of native soft tissue, thereby minimizing the possibility of post-operative complications.

In some embodiments, as is provided in more detail herein below, an implantable magnetic device is introduced into the arytenoid cartilage of the subject, independent of a magnetic piston that is fixated to the thyroid cartilage of the subject. A custom needle tip found on this magnetic implant is a unique design that provides a fully reversible locking mechanism. The amount of tissue stress created by the presently disclosed implant is significantly less than larger screw systems, which provide permanent mechanical fixation to the external thyroid cartilage components.

Referring now to FIG. 1 is a block diagram of an example of the presently disclosed magnetic vocal fold manipulator system 100 that includes a magnetics-based thyroid cartilage implant 110 and a magnetics-based arytenoid cartilage implant 120. Magnetics-based thyroid cartilage implant 110 is designed for implanting in or otherwise affixed to the thyroid cartilage of a subject. The thyroid cartilage comprises the bulk of the front wall of the larynx and protects the vocal folds, i.e., the vocal cords, which are located directly behind it. Magnetics-based arytenoid cartilage implant 120 is designed for implanting in or otherwise affixed to the arytenoid cartilage of a subject. The arytenoid cartilages are paired cartilages that form a part of the larynx to which the vocal folds are attached. The arytenoid cartilages influence the position and tension of the vocal folds, which allows and facilitates vocal fold movement. The arytenoid cartilages are located at the posterosuperior border of the cricoid cartilage of the larynx.

One feature of magnetic vocal fold manipulator system 100 is that the main interaction between magnetics-based thyroid cartilage implant 110 and magnetics-based arytenoid cartilage implant 120 is by magnetic force. In one example, magnetics-based thyroid cartilage implant 110 includes a magnet and magnetics-based arytenoid cartilage implant 120 is formed of a magnetically responsive material. Accordingly, magnetic force is used to pull magnetics-based arytenoid cartilage implant 120 that is implanted in the arytenoid cartilage toward magnetics-based thyroid cartilage implant 110 that is implanted in the thyroid cartilage. In so doing, the arytenoid cartilage, which is mechanically fixated to magnetics-based arytenoid cartilage implant 120, then lateralizes to provide airway patency. More details of a representative, non-limiting example of magnetics-based thyroid cartilage implant 110 are shown and described herein below with reference to FIG. 2, FIG. 3, and FIG. 4. More details of a representative, non-limiting example of magnetics-based arytenoid cartilage implant 120 are shown and described herein below with reference to FIG. 5, FIG. 6, and FIG. 7.

Because the interaction between magnetics-based thyroid cartilage implant 110 and magnetics-based arytenoid cartilage implant 120 is by magnetic force and not mechanical coupling, the amount of tissue stress created by these implants is significantly less than conventional larger screw systems that provide permanent mechanical fixation to the external thyroid cartilage components. Namely, in magnetic vocal fold manipulator system 100, the line of action of the magnetic force can act across soft tissue without disrupting its integrity and reducing the risk of potential fistula formation.

Magnetic vocal fold manipulator system 100 also includes an implant introducer device 130. Implant introducer device 130 is any instrument for introducing and/or manipulating magnetics-based thyroid cartilage implant 110 and/or magnetics-based arytenoid cartilage implant 120 during the vocal fold manipulation procedure. More details of an example of implant introducer device 130 are shown and described herein below with reference to FIG. 8 and FIG. 24.

Referring now to FIG. 2, FIG. 3, and FIG. 4 is an exploded side view, an exploded perspective view, and a perspective view, respectively, of a magnetic thyroid cartilage implant 200, which is an example of the magnetics-based thyroid cartilage implant 110 shown in FIG. 1. Additionally, FIG. 4 shows magnetic thyroid cartilage implant 200 when assembled and as it would lie within the thyroid cartilage.

Referring now to FIG. 2, magnetic thyroid cartilage implant 200 includes, for example, a magnet 210 installed, housed, or otherwise enclosed in a hollow tubular body 220, e.g., an external casing. Magnet 210 can be a permanent magnet or an electromagnet. In particular embodiments, magnet 210 comprises a neodymium magnet. In more particular embodiments, magnet 210 comprises an alloy of neodymium, iron, and boron. In yet more particular embodiments, magnet 210 comprises a $Nd_2Fe_{14}B$ tetragonal crystalline structure. In other embodiments, the magnet 210 comprises a magnetic material selected from the group consisting of $SmCo_5$, Sm $(Co, Cu, Zr)_7$, AlNiCo, and Sr-ferrite. Regarding embodiments wherein magnet 210 comprises an electromagnet, specific embodiments include, but are not limited to, ferromagnetic centers wound with a solenoid wire. These include systems that may be driven by either direct or alternating currents.

Body 220 is a hollow tubular body that has a slotted end 222 and a non-slotted end 224. Together, magnet 210 and body 220 form the magnetic component of magnetic thyroid cartilage implant 200 (i.e., the thyroid cartilage implant) that will interact with magnetics-based arytenoid cartilage implant 120 (e.g., the example shown FIG. 5, FIG. 6, and FIG. 7). FIG. 17 illustrates a side view and a perspective view showing more details of body 220 of magnetic thyroid cartilage implant 200, which is a non-threaded body. In one example, body 220 has an overall length L of between about 10 mm and about 20 mm, including 10, 11, 12, 13, 14, 15, 16, 17, 18, 19, and 20 mm, and in particular embodiments has a length of about 15.3 mm, and an outside diameter (OD) of between about 2 mm and about 6 mm, including 2, 3, 4, 5, and 6 mm, and in particular embodiments has an OD of about 4.1 mm. FIG. 18 illustrates a side view and a perspective view of another example of body 220 of magnetic thyroid cartilage implant 200. In this example, body 220 is a threaded body. For example, non-slotted end 224 has threads 225 thereon. Threads 225 may engage with corresponding threads (not shown) of translational bushing 230. Body 220 can be comprised of any inert non-magnetic medical grade material that includes, but is not limited to, cobalt-chrome, stainless steel, titanium, or medical grade polymers and silicone with suitable stiffness.

Referring once again to FIG. 2 and FIG. 3, body 220 is seated within a translational bushing 230. Translational bushing 230 is a hollow tubular bushing that has a slotted end 232 and a threaded end 234. In some embodiments, threaded end 234 of translational bushing 230 comprises male threads. FIG. 19 illustrates a side view and a perspective view showing more details of translational bushing 230 of magnetic thyroid cartilage implant 200. In one example, translational bushing 230 has an overall length L of between about 5 mm to about 10 mm, including 5, 6, 7, 8, 9, and 10 mm, and in particular embodiments has as length of about 7.3 mm, and an outside diameter (OD) of between about 2.5 to about 8.5 mm, including 2.5, 3, 3.5, 4, 4.5, 5, 5.5, 6, 6.5, 7, 7.5, 8, and 8.5 mm, and in particular embodiments has an OD of 5.5 mm. Translational bushing 230 can be made from any suitable material. In some embodiments, translational bushing 230 comprises a material selected from the group consisting of cobalt-chrome, stainless steel, and titanium. Other suitable materials include inert medical grade polymers and silicone with suitable stiffness.

Threaded end 234 of translational bushing 230 is screwed into or otherwise mated with an anchoring flange 240. Anchoring flange 240 is a hollow tubular flange that has threads 242 on the inside, i.e., on an inner surface thereof, of the flange (see FIG. 3). In some embodiments, threads 242 on the inside of anchoring flange 240 comprise female threads. In such embodiments, the female threads of anchoring flange 240 are mated with the male threads of translational bushing 230. There is a rim 244 near and around the end of anchoring flange 240 that receives translational bushing 230. There is a rim 246 near and around the end of anchoring flange 240 farthest from translational bushing 230. FIG. 20 illustrates a side view and a perspective view showing more details of anchoring flange 240 of magnetic thyroid cartilage implant 200. In one example, anchoring flange 240 has an overall length L of between about 3 to about 10 mm, including 3, 4, 5, 6, 7, 8, 9, and 10 mm, and in particular embodiments has a length of about 6.3 mm, Further, the main body of anchoring flange 240 has an outside diameter (OD) of between about 5 mm to about 10 mm, including 5, 6, 7, 8, 9, and 10 mm, and in particular embodiments has an OD of about 8 mm. Body 220, translational bushing 230, and anchoring flange 240 can be formed, for example, of cobalt-chrome (CoCr), stainless steel, titanium (Ti), medical grade plastic, medical grade silicone, and the like. In particular embodiments, anchoring flange 240 comprises a polyethylene material, for example, ultrahigh molecular weight polyethylene (UHMWPE). In other embodiments, anchoring flange 240 may be comprised of appropriately stiff medical grade silicone.

When in use, anchoring flange 240 is fastened into an iatrogenic hole, e.g., a hole that can be created by a surgeon or other medical personnel, which is introduced on the lateral aspect of the thyroid cartilage of the subject. Because translational bushing 230 is threaded, adjustments within anchoring flange 240 can be made to alter the relative depth of translational bushing 230 within anchoring flange 240. This feature allows the depth or position of magnet 210 to be altered within magnetic thyroid cartilage implant 200 and, when in use, in relation to magnetized or magnetizable arytenoid locking screw 300. Referring now again to FIG. 4, note that, in some embodiments, the slot of slotted end 222 of body 220 is aligned with the slot of slotted end 232 of translational bushing 230 so that both can be engaged with, for example, a screwdriver blade at one time and rotated together.

Referring now to FIG. 5, FIG. 6, and FIG. 7 is a perspective view, a side view, and a front view, respectively, of an implantable magnetized arytenoid locking screw 300, which is an example of the magnetics-based arytenoid cartilage implant 120 shown in FIG. 1. Magnetized arytenoid locking screw 300 is an implantable locking screw. Magnetized arytenoid locking screw 300 includes a shaft 310, a beveled and hollowed tip 312 mounted on one end of shaft 310, and a slotted flange 314 on the opposite end of shaft 310. In one example and referring now to FIG. 6, magnetized arytenoid locking screw 300 has an overall length L of between about 8 mm to about 16 mm, including 8, 9, 10, 11, 12, 13, 14, 15, and 16 mm, and in particular embodiments has a length of about 12.5 mm, and an outside diameter (OD) of between about 2 mm to about 8 mm, including 2, 3, 4, 5, 6, 7, and 8 mm, and in particular embodiments has an OD of about 4.9 mm.

Tip 312 of magnetized arytenoid locking screw 300 is a unique design (i.e., beveled and hollowed) that provides a fully reversible locking mechanism. For example, tip 312 allows for mechanical fixation of the implantable magnetized arytenoid locking screw 300 within cartilaginous tissue by rotating it about 90 degrees in one direction (e.g., counterclockwise (CCW), the hollow opening rotating toward or into the tissue). Similarly, magnetized arytenoid locking screw 300 can be unlocked by rotating it about 90 degrees in the reverse direction (e.g., clockwise (CW), the hollow opening rotating away from or out of the tissue). FIG. 21 illustrates a perspective view, a side view, and an end view showing more details of the tip portion (e.g., tip 312) of arytenoid locking screw 300 shown in FIG. 5, FIG. 6, and FIG. 7. FIG. 22 illustrates a perspective view and a side view showing more details of the slotted flange portion (e.g., slotted flange 314) of arytenoid locking screw 300 shown in FIG. 5, FIG. 6, and FIG. 7. FIG. 23 illustrates perspective views and a side view of another example of arytenoid locking screw 300. In this example, tip 312 is a conical smooth tip. Further, threads 315 are provided around shaft 310 of this example of arytenoid locking screw 300.

The implantable magnetized arytenoid locking screw 300 can be inserted into or otherwise affixed onto the arytenoid cartilage via a translaryngeal or transcervical approach using conventional microlaryngeal techniques known in the art. It is embedded into the ipsilateral arytenoid cartilage underneath its overlying mucosal lining. Rather than spanning a full 360 degrees, tip 312 of magnetized arytenoid locking screw 300 consists of two 90-degree sections that can be found on complementary sides as shown in FIG. 7. FIG. 6 shows the hollow nature of tip 312, which enables magnetized arytenoid locking screw 300 to mechanically grasp soft tissue by turning about 90 degrees after being inserted. This unique design of magnetized arytenoid locking screw 300 also allows for a fully reversible mechanical fixation. For example, by rotating magnetized arytenoid locking screw 300 in the opposite direction by about 90 degrees, the soft tissue is no longer encased in the hollow tip 312 and the entire component can be removed.

The main interaction between magnetic thyroid cartilage implant 200 and magnetized arytenoid locking screw 300 is through magnet 210 and the magnetized arytenoid locking screw 300 itself. As the locking screw 300 itself is magnetized (either through the magnetic nature of its material or the incorporation of a smaller magnet into screw 300, for example, in shaft 310), the magnetic force of magnet 210 pulls magnetized arytenoid locking screw 300 toward magnetic thyroid cartilage implant 200. In so doing, the arytenoid cartilage, which is mechanically fixated to magnetized arytenoid locking screw 300, then lateralizes to provide airway patency.

The strength of the magnetic force between magnetic thyroid cartilage implant 200 and magnetized arytenoid locking screw 300 is adjustable by adjusting the physical distance between magnet 210 of magnetic thyroid cartilage implant 200 and magnetized arytenoid locking screw 300. Namely, the magnetic force can be altered by adjusting the depth at which magnet 210 is placed within anchoring flange 240 of magnetic thyroid cartilage implant 200. Translational bushing 230 is externally threaded (e.g., threaded end 234) and can therefore move axially relative to anchoring flange 240 (which has internal threads 242). This axial translation provides the user the ability to adjust how closely magnet 210 is positioned with respect to slotted flange 314 of magnetized arytenoid locking screw 300 and as a result directly affect the magnetic force at magnetized arytenoid locking screw 300. This magnetic force is inversely proportional to the square of the distance between magnet 210 and the magnetized surface of magnetized arytenoid locking screw 300. This relationship allows small adjustments in distance to create a meaningful change in magnetic force. The amount of lateralization also is being affected by this same mechanism. More details of a method of using magnetic thyroid cartilage implant 200 and magnetized arytenoid locking screw 300 are described herein below with reference to FIG. 9 through FIG. 16.

Referring now to FIG. 8 is a side view of a vocal fold lateralization device introducer 400, which is an example of the implant introducer device 130 shown in FIG. 1. Vocal fold lateralization device introducer 400 can be used when implanting magnetic thyroid cartilage implant 200 and/or magnetized arytenoid locking screw 300. For example, vocal fold lateralization device introducer 400 is used to stabilize the operator's hand while implanting magnetic thyroid cartilage implant 200 into thyroid cartilage and/or implanting magnetized arytenoid locking screw 300 into arytenoid cartilage. Namely, vocal fold lateralization device introducer 400 is a custom instrument that is designed to assist in the manipulation of magnetized arytenoid locking screw 300.

Referring now to FIG. 24 is a perspective view and a side view of another example of vocal cord lateralization device introducer 400. Again, vocal cord lateralization device introducer 400 includes handle grip 410 that is operatively coupled to elongated hollow chamber 412. Additionally, a slot 413 is provided at the tip of elongated hollow chamber 412.

Vocal fold lateralization device introducer 400 includes a handle grip 410 that is operatively coupled to an elongated hollow chamber 412 that houses a custom screwdriver 414 and magnetized or magnetizable arytenoid locking screw 300.

The manipulation of all the aforementioned components of magnetic thyroid cartilage implant 200 and/or magnetized arytenoid locking screw 300 can be achieved through use of custom screwdrivers. Namely, elongated hollow chamber 412 houses custom screwdriver 414 and magnetized arytenoid locking screw 300 as it is passed via a translaryngeal or transcervical approach to engage the underlying cartilage. Additionally, using vocal fold lateralization device introducer 400, magnetic thyroid cartilage implant 200 can be adjusted by engaging slotted end 222 of body 220 through the use of a slot head custom screwdriver 414. Additionally, magnetized arytenoid locking screw 300 and/or translational bushing 230 of magnetic thyroid cartilage implant 200 can be adjusted using custom screwdriver 414, either a flattened Phillips head (FIG. 25) or slot head (FIG. 26).

Referring now to FIG. 25 is a side view and a perspective view of an example of custom screwdriver 414 for use with vocal cord lateralization device introducer 400. In this example, the tip includes a cross blade configuration. Referring now to FIG. 26 is a side view and a perspective view of another an example of custom screwdriver 414 for use with vocal cord lateralization device introducer 400. In this example, the tip includes a single blade configuration. Referring now to FIG. 27 is a side view and a perspective view of an example of a custom puncture tool 900 for use with vocal cord lateralization device introducer 400. Custom puncture tool 900 will serve to create a pilot hole for the introduction of arytenoid screw 300 into the appropriate location, allowing easier engagement of the locking mechanism and screw head.

Again, because the interaction between magnetic thyroid cartilage implant 200 and magnetized arytenoid locking screw 300 is by magnetic force and not mechanical coupling, the amount of tissue stress created by these implants is significantly less than conventional larger screw systems that provide permanent mechanical fixation to the external thyroid cartilage components. Namely, in magnetic vocal fold manipulator system 100, the line of action of the magnetic force can act across soft tissue without disrupting its integrity and reducing the risk of potential fistula formation.

In some embodiments, the presently disclosed subject matter provides a kit for manipulating a position of a vocal fold, comprising the thyroid cartilage implant and the magnetics-based arytenoid cartilage implant described hereinabove. In certain embodiments, the kit further comprises an implant introducer device. In more certain embodiments, the kit further comprises one or more components selected from one or more custom screwdrivers, a custom puncture tool, and instructions for use. The kit can further comprise sterile packaging.

Referring now to FIG. 9 is a flow diagram of an example of a method 500 of using the presently disclosed magnetic vocal fold manipulator system 100 to perform lateralization and/or medialization of the vocal cord. Namely, method 500 describes a process of implanting the magnetic thyroid cartilage implant 200 and the magnetized arytenoid locking screw 300. Additionally, the entire process of method 500 is performed under direct visualization to confirm placement of the magnetic thyroid cartilage implant 200 and/or magnetized arytenoid locking screw 300. For example, visualization can be via translaryngeal endoscopy. Further, FIG. 10 through FIG. 16 may be referenced in the steps of method 500. Method 500 may include, but is not limited to, the following steps.

At a step 510, magnetized arytenoid locking screw 300 is introduced into the arytenoid cartilage via a translaryngeal or transcervical approach. For example and referring now to FIG. 10, a front view is provided of a subject 600 of a vocal fold manipulation procedure. FIG. 10 shows an example of an incision 610 in the neck of subject 600 through which the procedure can be performed. Using a microscope and conventional microlaryngeal techniques, a small mucosal flap is raised over the ipsilateral arytenoid complex. In some embodiments, the arytenoid screw may be implanted into the arytenoid cartilage via a transcervical approach. In such embodiments, a transcervically accessed hole through the thyroid cartilage is enlarged to directly place the arytenoid screw into the underlying arytenoid cartilage. In this fashion, the arytenoid screw will remain submucosal during its implantation as it does not penetrate the endoluminal aspect of the mucosa. In certain embodiments, confirmation for placement of this arytenoid screw is performed through direct visualization of the glottis from above using an operating laryngoscope and operating microscope.

Next, vocal fold lateralization device introducer 400 and custom screwdriver 414 shown in FIG. 8 may be used to manipulate magnetized arytenoid locking screw 300 and fix it into the cartilage. For example, elongated hollow chamber 412 houses the custom screwdriver 414 and magnetized arytenoid locking screw 300 as it is passed via a translaryngeal approach to engage the underlying cartilage.

Figure 11:
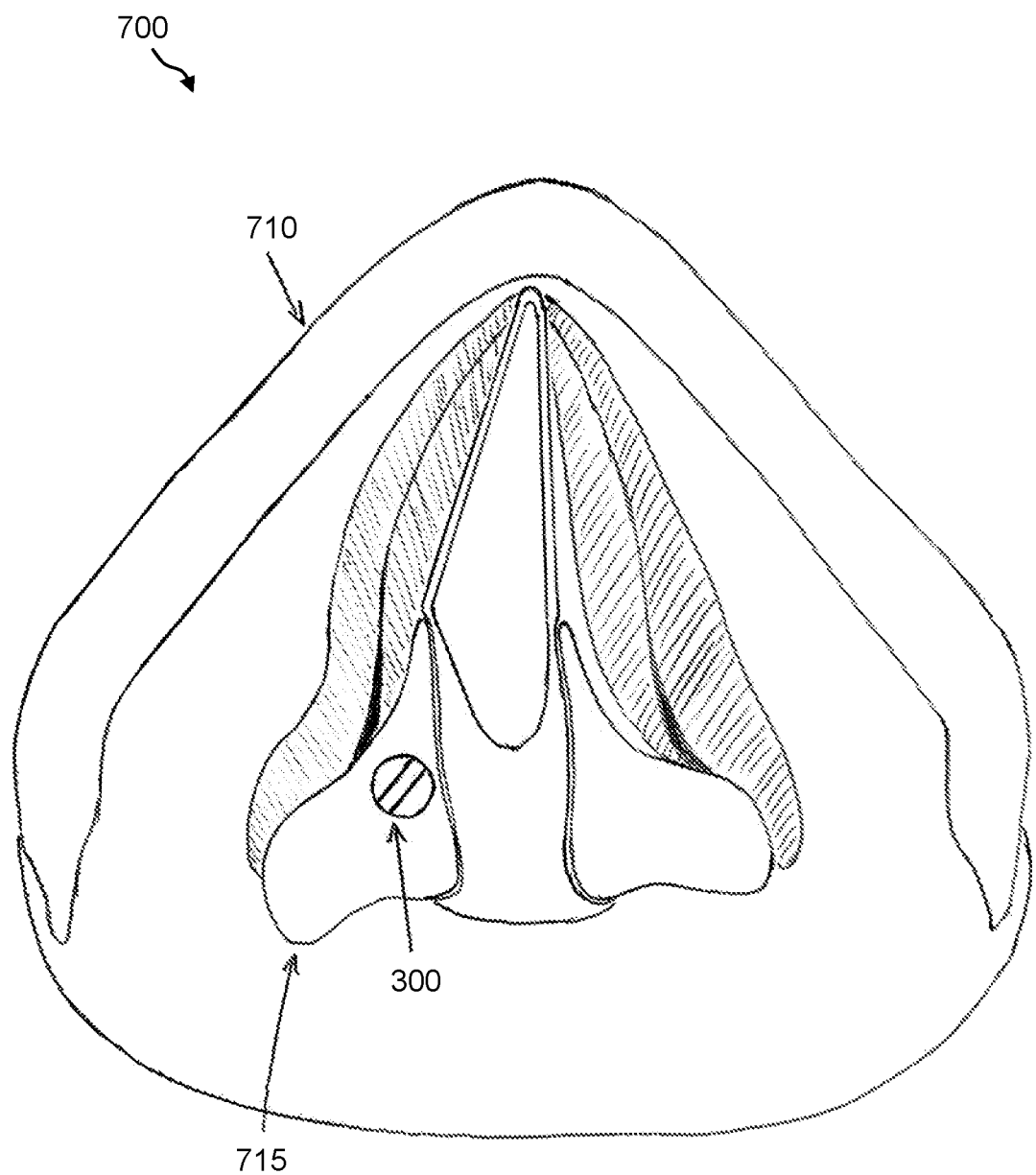
Figure 12:
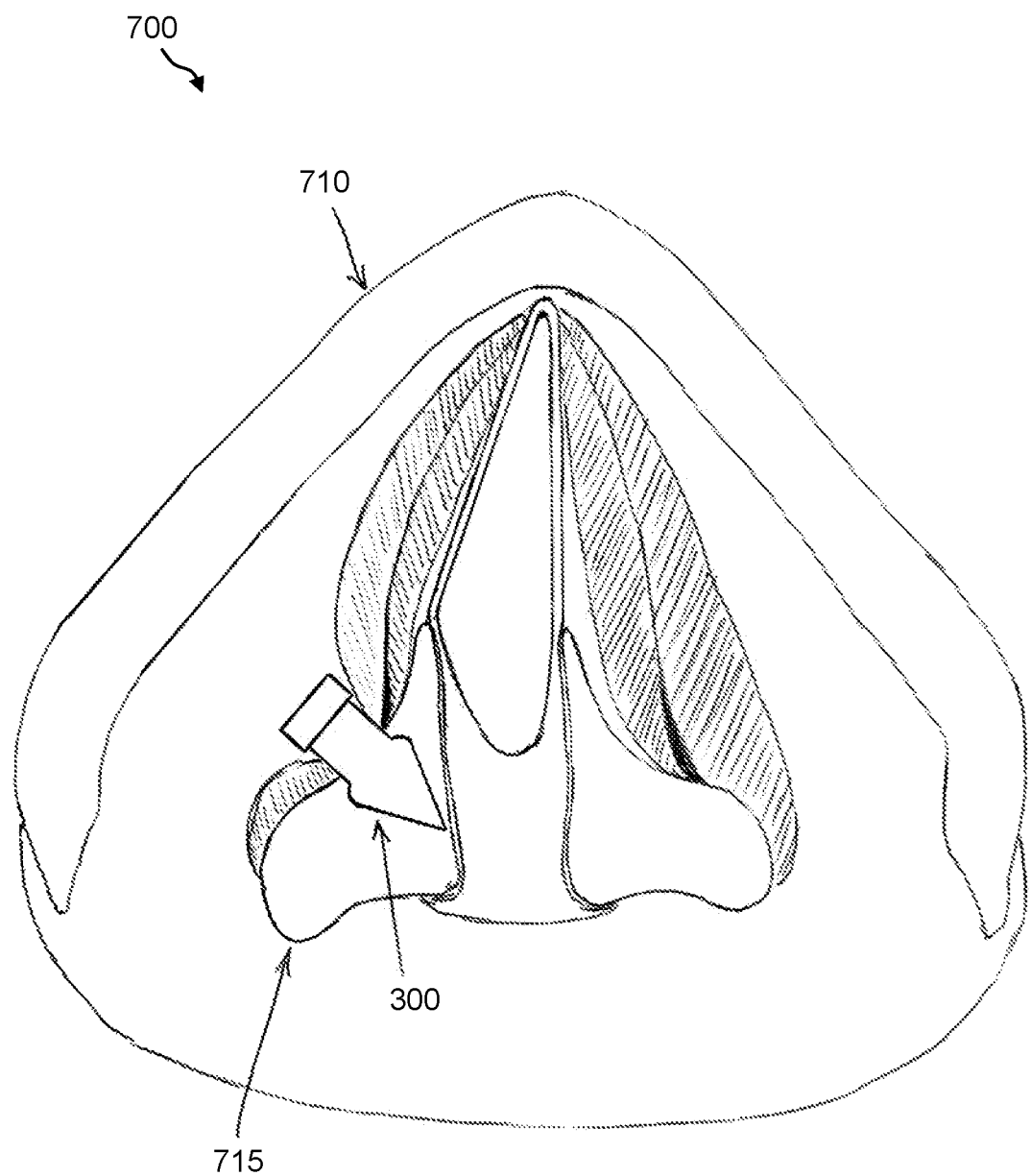

At a step 512, magnetized arytenoid locking screw 300 is rotated by about 90 degrees to mechanically fix it within the arytenoid cartilage. Next, vocal fold lateralization device introducer 400 and custom screwdriver 414 is removed. Example views of magnetized arytenoid locking screw 300 implanted in the arytenoid cartilage are shown in FIG. 11 and FIG. 12. Namely, FIG. 11 and FIG. 12 show vocal anatomy 700 that includes thyroid cartilage 710 and arytenoid cartilage 715 and wherein magnetized arytenoid locking screw 300 is implanted in arytenoid cartilage 715.

Figure 13:
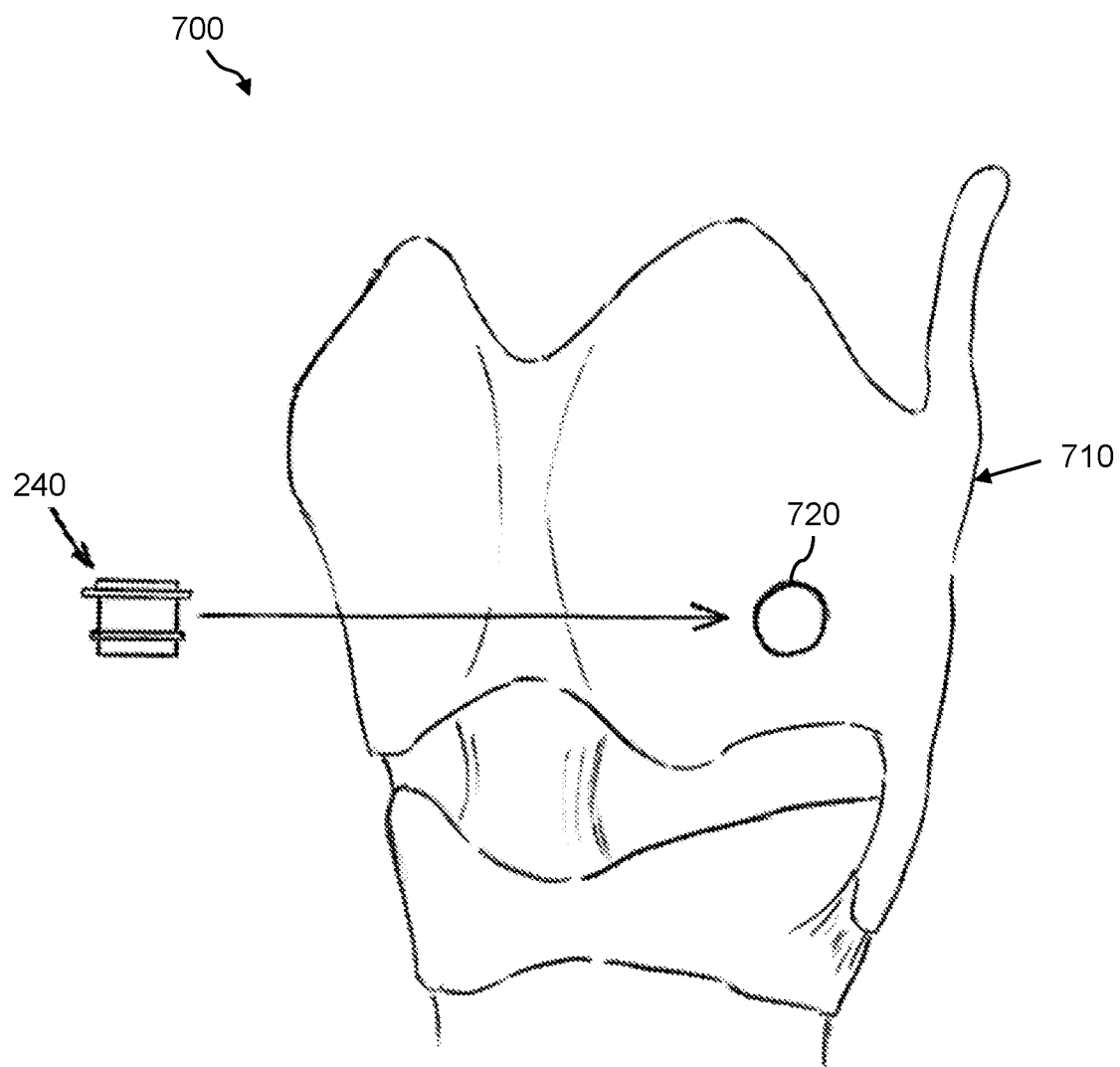
Figure 14:
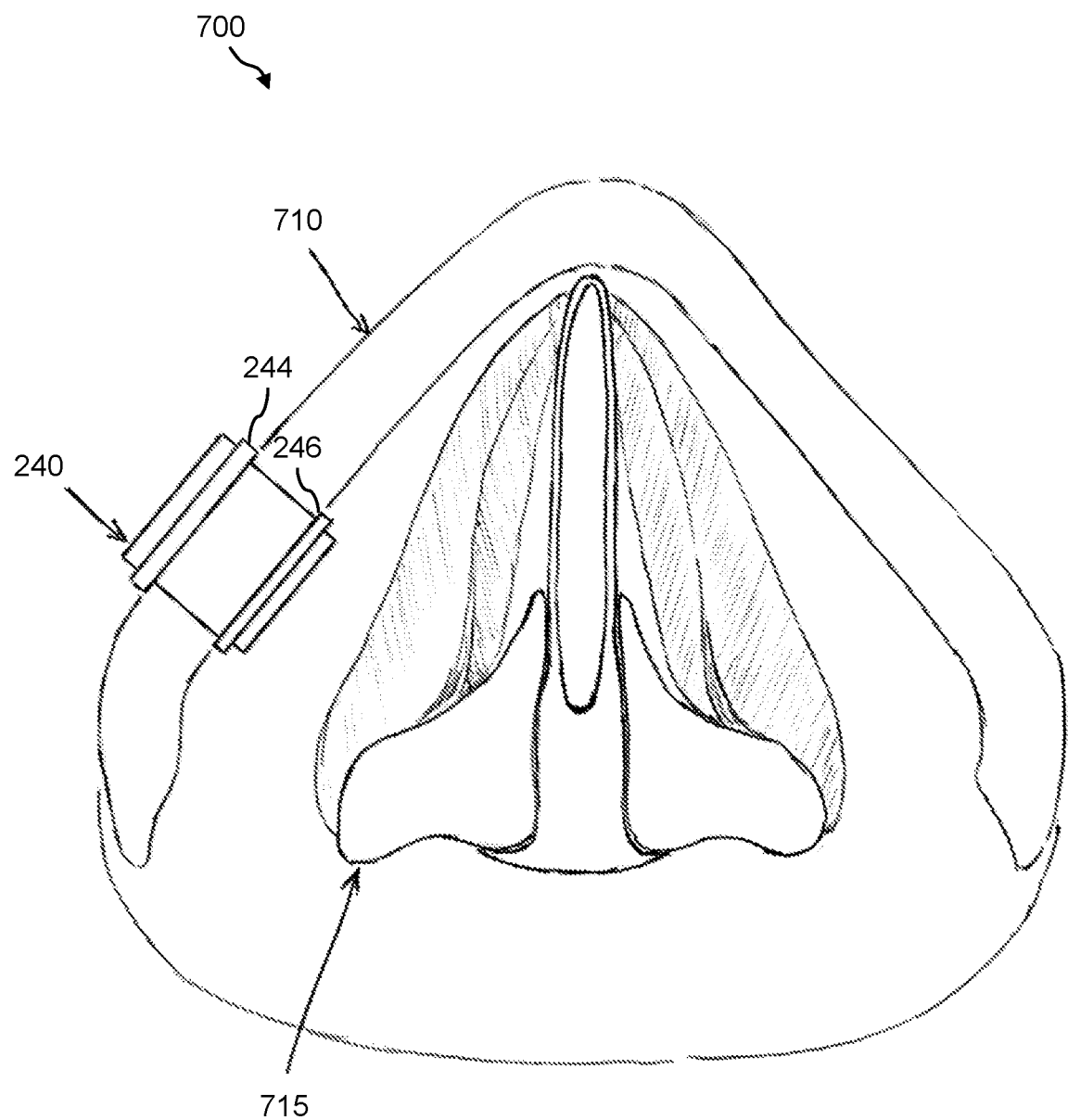

At a step 514, after placement of the magnetized arytenoid locking screw 300 has been visually confirmed, magnetic thyroid cartilage implant 200 is introduced into the iatrogenic opening of the thyroid cartilage. For example, anchoring flange 240 of magnetic thyroid cartilage implant 200 is mechanically fixed into an iatrogenic opening 720 of the thyroid cartilage 710 as shown in FIG. 13. Rim 244 and rim 246 of anchoring flange 240 assist in holding magnetic thyroid cartilage implant 200 securely in the thyroid cartilage 710 as shown in FIG. 14.

At a step 516, translational bushing 230 of magnetic thyroid cartilage implant 200 is screwed into anchoring flange 240 of the magnetic thyroid cartilage implant 200 to the desired depth, all while being visualized.

Figure 15:
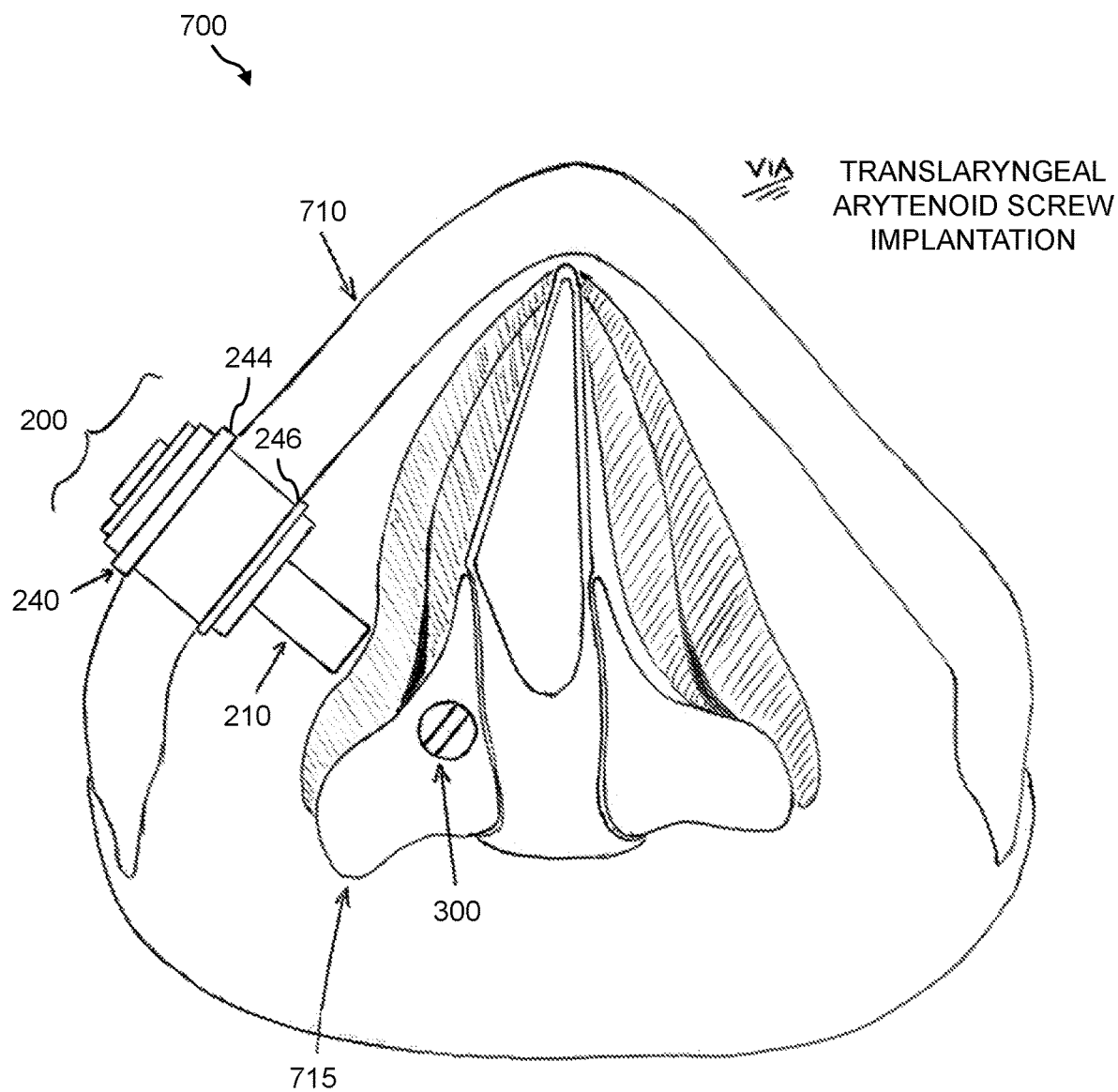
Figure 16:
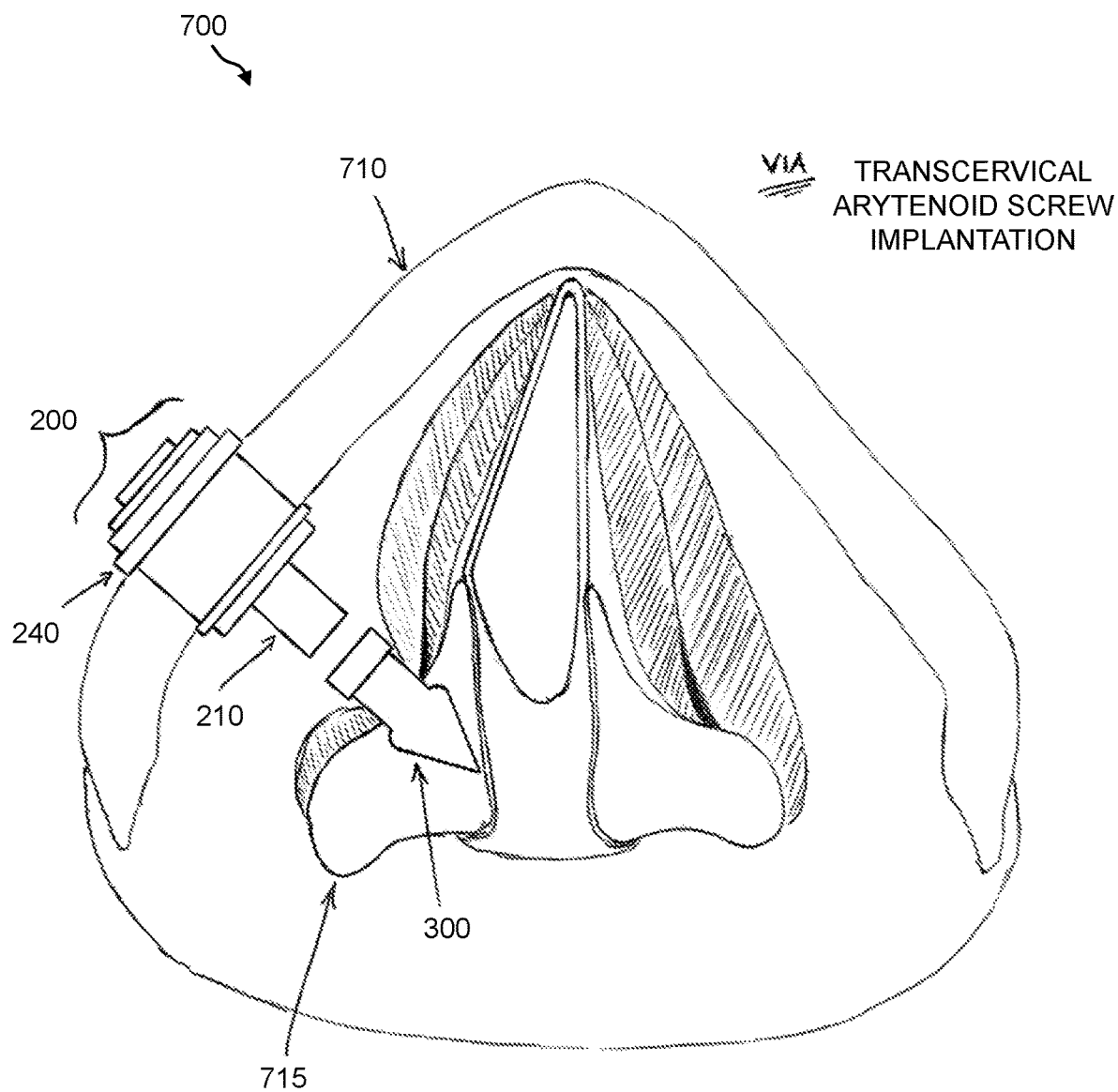

At a step 518, body 220 of magnetic thyroid cartilage implant 200 that holds magnet 210 is press-fit into slotted end 232 of translational bushing 230 of magnetic thyroid cartilage implant 200, as shown in FIG. 15, and thereby magnetically engage magnetic thyroid cartilage implant 200 with slotted flange 314 of magnetized arytenoid locking screw 300, as shown in FIG. 16. In this step, the use of magnetic force instead of mechanical interaction between this trans-cervical component (i.e., magnetic thyroid cartilage implant 200) and magnetized arytenoid locking screw 300 can reduce or entirely eliminate the possibility of fistula formation or disengagement of magnetized arytenoid locking screw 300.

At a step 520, the placement of magnetic thyroid cartilage implant 200 with respect to magnetized arytenoid locking screw 300 is confirmed visually using, for example, translaryngeal endoscopy and wherein the depth of translational bushing 230 in anchoring flange 240 may be adjusted until the appropriate amount of vocal fold lateralization is achieved.

In embodiments directed to medialization, the polarity of the multi-component device (preferably magnet 210) can be reversed to push the implanted magnetic device medially and as a result, medialize the vocalis process. The amount of lateralization and/or medialization will be optimized based on a particular subject's need with options to implant magnets of differing strengths and polarity to achieve the desired result.

In summary and referring again to FIG. 1 through FIG. 16, the presently disclosed magnetic vocal fold manipulator system 100 and method 500 can be used to manipulate (lateralization and/or medialization) the vocal cord(s) in those with permanent vocal fold paralysis. Magnetics-based thyroid cartilage implant 110 and magnetics-based arytenoid cartilage implant 120 are fully adjustable, allowing the final position of the vocal cord to be modified to maximize the quality of the patient's voice following the procedure. For example, magnetics-based thyroid cartilage implant 110 is provided that includes a magnet is inserted through the thyroid cartilage and magnetics-based arytenoid cartilage implant 120 is provided that is magnetically responsive and can reversibly move the vocal process region of the arytenoid cartilage. The interaction of magnetics-based thyroid cartilage implant 110 and magnetics-based arytenoid cartilage implant 120 by magnetic force allows for the lateralization of the arytenoid. In the case of medialization, the polarity of the magnet in magnetics-based thyroid cartilage implant 110 can be reversed in order to push magnetics-based arytenoid cartilage implant 120 medially and as a result, medialize the vocalis process. The amount of lateralization/medialization can be optimized based on patient need with options to implant magnets of differing strengths and polarity to achieve the desired result. Additionally, the presently disclosed magnetic vocal fold manipulator system 100 and method 500 is fully adjustable, fully reversible, and greatly reduces the amount of tissue stress at the cricoarytenoid joint.

In still yet other embodiments, an electromagnetic component can allow the presently disclosed magnetic vocal fold manipulator system 100 and method 500 to be used in conjunction with laryngeal pacing technology, thus allowing for dynamic vocal fold motion in those with paralysis even without an intact peripheral neural pathway and/or end muscle atrophy. Currently, laryngeal pacing (see, e.g., U.S. Pat. No. 7,069,082B2, for Pacemaker for Bilateral Vocal Cord Autoparalysis, to Lindenthaler, issued Jun. 27, 2006, which is incorporated herein by reference in its entirety)) only allows for restoration of movement in patients with an intact peripheral neural pathway or via direct muscle stimulus. The addition of this technology as an adjunct to a laryngeal pacer would therefore allow dynamic vocal fold motion in a larger patient population. Moreover, the presently disclosed magnetic vocal fold manipulator system 100 and method 500 may prove to be a more clinically effective model than conventional methods. Although the feasibility of these pacing devices has been demonstrated, there has not been significant improvement in patient voice outcomes using their implantation alone.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Cummings, C. W., E. E. Redd, W. H. Westra, and P. W. Flint. "Minimally Invasive Device to Effect Vocal Fold Lateralization." Ann Otol Rhinol Laryngol. 108.9 (1999): 833-36.

Cummings, C. W., P. W. Flint, and P. J. Scranton. Vocal Cord Lateralization and Medialization Device and Method. U.S. Pat. No. 5,593,439 A. 14 Jan. 1997.

Mueller A H, Hagen R, Foerster G, Grossmann W, Baumbusch K, Pototschnig C. Laryngeal pacing via an implantable stimulator for the rehabilitation of subjects suffering from bilateral vocal fold paralysis: A prospective first-in-human study. Laryngoscope 2016; 126:1810-1816.

Li Y, Garrett G, Zealear D. Current Treatment Options for Bilateral Vocal Fold Paralysis: A State-of-the-Art Review. Clin Exp Otorhinolaryngol 2017; 10:203-212.

Noriyuki O, Kuratani T, Hagihira S, Kazumi K I, Kaneko M, Mori T. Vocal cord paralysis after aortic arch surgery: Predictors and clinical outcome. Journal of Vascular Surgery. 2006 April; 43 (4): 721-728.

Young V, Zullo T, and Rosen C: Analysis of Laryngeal Framework Surgery: 10-Year Follow-up to a National Survey. Laryngoscope, 120:1602-1608, 2010

Sulica L, and Blitzer A: Preface in Vocal Fold Paralysis ed Sulica L and Blitzer A Springer New York 2006

Although the foregoing subject matter has been described in some detail by way of illustration and example for purposes of clarity of understanding, it will be understood by those skilled in the art that certain changes and modifications can be practiced within the scope of the appended claims That which is claimed:

1. A device for manipulating a position of a vocal fold of a subject comprising:
   (a) a thyroid cartilage implant comprising a magnet housed in a body, wherein the body is seated within a translational bushing mated to an anchoring flange, wherein the body comprises a hollow tubular body having a slotted end and an opposite non-slotted end, wherein the anchoring flange is adapted to be affixed to a thyroid cartilage of the subject; and
   (b) an arytenoid screw adapted to be affixed to an arytenoid cartilage of the subject.

2. The device of claim 1, wherein the magnet can be a permanent magnet or an electromagnet.

3. The device of claim 2, wherein the permanent magnet comprises a neodymium magnet.

4. The device of claim 1, wherein the translational bushing comprises a hollow tubular bushing having a slotted end and an opposite threaded end.

5. The device of claim 4, wherein the opposite threaded end of the translational bushing comprises a plurality of male threads adapted for mating with the anchoring flange.

6. The device of claim 1, wherein the anchoring flange comprises a hollow tubular flange having a plurality of threads on an inner surface thereof.

7. The device of claim 6, wherein the plurality of threads on the inner surface of the anchoring flange comprise female threads adapted for mating with the translational bushing.

8. The device of claim 1, wherein the translational bushing is adapted to move axially with respect to the anchoring flange.

9. The device of claim 1, wherein one or more of the body, the translational bushing, and the anchoring flange comprises a material selected from a group consisting of cobalt-chrome, stainless steel, titanium, a polymeric material, and medical grade silicone.

10. The device of claim 1, wherein the arytenoid screw comprises one or more components selected from a group consisting of a shaft, a beveled and hollowed tip mounted on one end of the shaft, and a slotted flange on an opposite end of the shaft.

11. The device of claim 10, wherein the beveled and hollowed tip further comprises two 90-degree sections on complementary sides thereof.

12. The device of claim 1, wherein the arytenoid screw comprises one or more of a magnetizable material or a magnet.

13. The device of claim 1, further comprising an implant introducer device.

14. The device of claim 13, wherein the implant introducer device comprises a handle grip operatively coupled to an elongated hollow chamber that houses a custom screwdriver.

15. The device of claim 14, wherein the custom screwdriver comprises a flattened Phillips head screwdriver or a slot head screwdriver.

16. The device of claim 14, wherein the elongated hollow chamber of the implant introducer device further comprises a magnetized or magnetizable arytenoid locking screw.

17. The device of claim 1, wherein the magnet comprises an electromagnet.

18. The device of claim 17, further comprising a laryngeal pacing system.

19. A kit for manipulating a position of a vocal fold, comprising the thyroid cartilage implant and the arytenoid screw of claim 1.

20. The kit of claim 19, further comprising an implant introducer device.

21. The kit of claim 19, further comprising one or more components selected from a group consisting of one or more custom screwdrivers, a custom puncture tool, and instructions for use.

22. A method for manipulating a position of a vocal fold of a subject, the method comprising:
   (a) providing a device for manipulating a position of a vocal fold of the subject; the device comprising a thyroid cartilage implant comprising a magnet housed in a body, wherein the body is seated within a translational bushing mated to an anchoring flange, wherein the anchoring flange is adapted to be affixed to a thyroid cartilage of the subject; and an arytenoid screw adapted to be affixed to an arytenoid cartilage of the subject;
   (b) implanting the thyroid cartilage implant in a thyroid cartilage of the subject;
   (c) implanting the arytenoid screw in an arytenoid cartilage of the subject; wherein implanting the arytenoid screw comprises raising a mucosal flap over an ipsilateral arytenoid complex of the subject and affixing the arytenoid screw to the arytenoid cartilage; and
   (d) adjusting a position of the magnet of the thyroid cartilage implant relative to the arytenoid screw to engage the arytenoid screw, thereby manipulating a position of the vocal fold of the subject.

23. The method of claim 22, wherein the arytenoid screw is implanted into the arytenoid cartilage via a translaryngeal or transcervical approach.

24. The method of claim 22, wherein the arytenoid screw is turned about 90 degrees to mechanically fix it to the arytenoid cartilage.

25. The method of claim 22, wherein the method is performed under direct visualization to confirm placement of the thyroid cartilage implant and/or arytenoid screw.

26. The method of claim 25, wherein the visualization is performed via translaryngeal endoscopy.

27. The method of claim 22, wherein implanting the thyroid cartilage implant into the thyroid cartilage of the subject comprises:
(a) mechanically affixing the anchoring flange to the thyroid cartilage through an iatrogenic opening of the thyroid cartilage;
(b) mating the translational bushing to the anchoring flange;
(c) fitting the body comprising the magnet into the translational bushing; and
(d) adjusting a position of the translational bushing relative to magnetically engage the arytenoid screw, thereby manipulating a position of the vocal fold of the subject.

28. The method of claim 22, further comprising reversing a polarity of the magnet to medialize the position of the vocal fold of the subject.

29. The method of claim 22, further comprising an electromagnet and a laryngeal pacing system for dynamic vocal fold manipulation.

30. A method for manipulating a position of a vocal fold of a subject, the method comprising:
(a) providing a device for manipulating a position of a vocal fold of the subject; the device comprising a thyroid cartilage implant comprising a magnet housed in a body, wherein the body is seated within a translational bushing mated to an anchoring flange, wherein the anchoring flange is adapted to be affixed to a thyroid cartilage of the subject; and an arytenoid screw adapted to be affixed to an arytenoid cartilage of the subject;
(b) implanting the thyroid cartilage implant in a thyroid cartilage of the subject;
wherein implanting the thyroid cartilage implant into the thyroid cartilage of the subject comprises: mechanically affixing the anchoring flange to the thyroid cartilage through an iatrogenic opening of the thyroid cartilage; mating the translational bushing to the anchoring flange; fitting the body comprising the magnet into the translational bushing; and adjusting a position of the translational bushing relative to magnetically engage the arytenoid screw, thereby manipulating a position of the vocal fold of the subject; and
(c) implanting the arytenoid screw in an arytenoid cartilage of the subject; and
(d) adjusting a position of the magnet of the thyroid cartilage implant relative to the arytenoid screw to engage the arytenoid screw, thereby manipulating a position of the vocal fold of the subject.

31. The method of claim 30, further comprising reversing a polarity of the magnet to medialize the position of the vocal fold of the subject.

32. A method for manipulating a position of a vocal fold of a subject, the method comprising:
(a) providing a device for manipulating a position of a vocal fold of the subject; the device comprising a thyroid cartilage implant comprising a magnet housed in a body, wherein the body is seated within a translational bushing mated to an anchoring flange, wherein the anchoring flange is adapted to be affixed to a thyroid cartilage of the subject; and an arytenoid screw adapted to be affixed to an arytenoid cartilage of the subject;
(b) implanting the thyroid cartilage implant in a thyroid cartilage of the subject;
(c) implanting the arytenoid screw in an arytenoid cartilage of the subject; and
(d) adjusting a position of the magnet of the thyroid cartilage implant relative to the arytenoid screw to engage the arytenoid screw, thereby manipulating a position of the vocal fold of the subject; further comprising reversing a polarity of the magnet to medialize the position of the vocal fold of the subject.

33. A device for manipulating a position of a vocal fold of a subject comprising:
a thyroid cartilage implant comprising a magnet housed in a body, wherein the body is seated within a translational bushing mated to an anchoring flange, wherein the anchoring flange is adapted to be affixed to a thyroid cartilage of the subject; and
an arytenoid screw adapted to be affixed to an arytenoid cartilage of the subject; and
an implant introducer device, wherein the implant introducer device comprises a handle grip operatively coupled to an elongated hollow chamber that houses a custom screwdriver.

34. The device of claim 33, wherein the custom screwdriver comprises a flattened Phillips head screwdriver or a slot head screwdriver.

35. The device of claim 33, wherein the elongated hollow chamber of the implant introducer device further comprises a magnetized or magnetizable arytenoid locking screw.

* * * * *